US007785805B2

(12) United States Patent
Friedman et al.

(10) Patent No.: US 7,785,805 B2
(45) Date of Patent: Aug. 31, 2010

(54) MAN2AS AS MODIFIERS OF THE IGFR PATHWAY AND METHODS OF USE

(75) Inventors: Lori Friedman, San Carlos, CA (US); Helen Francis-Lang, San Francisco, CA (US); Annette L. Parks, Newton, MA (US); Kenneth James Shaw, Brisbane, CA (US); HaiGuang Zhang, El Sobrante, CA (US); Timothy S. Heuer, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 709 days.

(21) Appl. No.: 10/587,253

(22) PCT Filed: Jan. 27, 2005

(86) PCT No.: PCT/US2005/003483

§ 371 (c)(1),
(2), (4) Date: Jun. 8, 2007

(87) PCT Pub. No.: WO2005/073725

PCT Pub. Date: Aug. 11, 2005

(65) Prior Publication Data

US 2007/0264268 A1 Nov. 15, 2007

Related U.S. Application Data

(60) Provisional application No. 60/539,837, filed on Jan. 28, 2004.

(51) Int. Cl.
*G01N 33/53* (2006.01)
(52) U.S. Cl. .................... 435/7.21; 435/2; 435/7.1; 436/501; 436/518; 436/522; 422/50; 422/61; 530/300; 530/350
(58) Field of Classification Search .......... None
See application file for complete search history.

(56) References Cited

U.S. PATENT DOCUMENTS

2002/0172670 A1 11/2002 Rose et al.

FOREIGN PATENT DOCUMENTS

WO WO 01/75067 A2 10/2001

OTHER PUBLICATIONS

Kang et al, Retinoic acid alters the intracellular trafficking of the mannose-6-phosphate/insulin-like growth factor Ii receptor and lysosomal enzymes. Proceedings of the National Academy of Sciences, USA, Cell Biology, vol. 95, Nov. 1998, pp. 13687-13691, see entire document.
Kang et al., Retinoic acid alters the intracellular trafficking of the mannose-6-phosphate/insulin-like growth factor Ii receptor and lysosomal enzymes. Proceedings of the National Academy of Sciences, USA, Cell Biology, vol. 98, Nov. 1998, pp. 13687-13691.
van den Elsen, Jean M. H. et al.: "Structure of Golgi alpha-mannosidase II: A target for inhibition of growth and metastasis of cancer cells," EMBO Journal, Oxford University Press, Surrey GB, vol. 20, No. 12, Jun. 15, 2001, pp. 3008-3017.
Goss, P.E. et al.: "Inhibitors of Carbohydrate Processing: A New Class of Anticancer Agents," Electronic and Computing Monthly, Clinical Cancer Research, vol. 1, Sep. 1995, pp. 935-944.
Goss, Paul E. et al.: "A phase I study of swainsonine in patients with advance malignancies," Cancer Research, vol. 54, No. 6, 1994, pp. 1450-1457.
Goss, Paul E. et al.: "Phase IB clinical trial of the oligosaccharide processing inhibitor swainsonine in patients with advance malignancies," Clinical Cancer Research, The American Association for Cancer Research, US, vol. 3, No. 7, Jul. 1997, pp. 1077-1086.
Kiess W. et al.: "Biosynthesis of the Insulin-Like Growth Factor-II IGF-II Mannose-6-Phosphatereceptor in RAT C6 Glial cells the role of N-Linked Glycosylation in Binding of IGF-II to the Receptor," Molecular Endocrinology, Baltimore, MD, US, vol. 5, No. 2, 1991, pp. 281-291.
Database EMBL [online] Sep. 6, 1995, Misumi Y.: *Homo sapiens* mRNA for golgi alpha-mannosidaseII, complete cds, Database Accession No. D63998.
Misago M. et al.: "Molecular cloning and expression of cDNAs encoding human alpha-mannosidaise II and a previously unrecognized alpha-mannosidase IIx isozyme," Proceedings of the National Academy of Sciences of USA, National Academy of Science, Washington, DC, US, vol. 92, Dec. 1995, pp. 11766-11770.
Zhao Hong et al.: "PTEN inhibits cell proliferation and induces apoptosis by downregulating cell surface IGF-IR expression in prostate cancer cells," Oncogene, vol. 23, No. 3, Jan. 22, 2004, pp. 786-794.

*Primary Examiner*—Lisa V Cook
(74) *Attorney, Agent, or Firm*—McDonnell Boehnen Hulbert & Berghoff LLP

(57) ABSTRACT

Human MAN2A genes are identified as modulators of the IGFR pathway and thus are therapeutic targets for disorders associated with defective IGFR function Methods for identifying modulators of IGFR comprising screening for agents that modulate the activity of MAN2A are provided.

16 Claims, No Drawings

MAN2AS AS MODIFIERS OF THE IGFR PATHWAY AND METHODS OF USE

REFERENCE TO RELATED APPLICATIONS

This application is a U.S. national phase application of PCT/U.S.2005/003483, filed Jan. 27, 2005, which claims priority to U.S. provisional patent application 60/539,837 filed Jan. 28, 2004. The contents of the prior application is hereby incorporated by reference in its entirety.

BACKGROUND OF THE INVENTION

Somatic mutations in the PTEN (Phosphatase and Tensin homolog deleted on chromosome 10) gene are known to cause tumors in a variety of human tissues. In addition, germline mutations in PTEN are the cause of human diseases (Cowden disease and Bannayan-Zonana syndrome) associated with increased risk of breast and thyroid cancer (Nelen M R et al. (1997) Hum Mol Genet, 8:1383-1387; Liaw D et al. (1997) Nat Genet, 1:64-67; Marsh D J et al. (1998) Hum Mol Genet, 3:507-515). PTEN is thought to act as a tumor suppressor by regulating several signaling pathways through the second messenger phosphatidylinositol 3,4,5 triphosphate (PIP3). PTEN dephosphorylates the D3 position of PIP3 and downregulates signaling events dependent on PIP3 levels (Maehama T and Dixon J E (1998) J Biol Chem, 22, 13375-8). In particular, pro-survival pathways downstream of the insulin-like growth factor (IGF) pathway are regulated by PTEN activity. Stimulation of the IGF pathway, or loss of PTEN function, elevates PIP3 levels and activates pro-survival pathways associated with tumorigenesis (Stambolic V et al. (1998) Cell, 95:29-39). Consistent with this model, elevated levels of insulin-like growth factors I and II correlate with increased risk of cancer (Yu H et al (1999) J Natl Cancer Inst 91:151-156) and poor prognosis (Takanami I et al, 1996, J Surg Oncol 61(3):205-8). In addition, increased levels or activity of positive effectors of the IGF pathway, such as Akt and PI(3) kinase, have been implicated in several types of human cancer (Nicholson K M and Anderson N G (2002) Cellular Signalling, 14:381-395).

In *Drosophila melanogaster*, as in vertebrates, the Insulin Growth Factor Receptor (IGFR) pathway includes the positive effectors PI(3) kinase, Akt, and PDK and the inhibitor, PTEN. These proteins have been implicated in multiple processes, including the regulation of cell growth and size as well as cell division and survival (Oldham S and Hafen E. (2003) Trends Cell Biol. 13:79-85; Garafolo R S. (2002) Trends Endocr. Metab. 13:156-162; Backman S A et al. (2002) Curr. Op. Neurobio. 12:1-7; Tapon N et al. (2001) Curr Op. Cell Biol. 13:731-737). Activation of the pathway in *Drosophila* can result in increases in cell size, cell number and organ size (Oldham S et al. (2002) Dev. 129:4103-4109; Prober D A and Edgar B A. (2002) Genes & Dev. 16:2286-2299; Potter C J et al. (2001) Cell 105:357-368; Verdu J et al. (1999) Cell Biol. 1:500-506).

Alpha-mannosidase II A (MAN2A), member of the glycosyl hydrolase family, is a Golgi enzyme that catalyzes the final hydrolytic step in the asparagine-linked oligosaccharide (N-glycan) maturation pathway, acting as the committed step in the conversion of high mannose to complex type structures. Mutations in the mouse homolog of MAN2A1 lead to a systemic autoimmune disease similar to human systemic lupus erythematosus. Mutations in the MAN2A2 gene in the male mice results in their infertility.

The ability to manipulate the genomes of model organisms such as *Drosophila* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as IGFR, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the IGFR pathway in *Drosophila*, and identified their human orthologs, hereinafter referred to as Alpha-mannosidase II A (MAN2A). The invention provides methods for utilizing these IGFR modifier genes and polypeptides to identify MAN2A-modulating agents that are candidate therapeutic agents that can be used in the treatment of disorders associated with defective or impaired IGFR function and/or MAN2A function. Preferred MAN2A-modulating agents specifically bind to MAN2A polypeptides and restore IGFR function. Other preferred MAN2A-modulating agents are nucleic acid modulators such as antisense oligomers and RNAi that repress MAN2A gene expression or product activity by, for example, binding to and inhibiting the respective nucleic acid (i.e. DNA or mRNA).

MAN2A modulating agents may be evaluated by any convenient in vitro or in vivo assay for molecular interaction with a MAN2A polypeptide or nucleic acid. In one embodiment, candidate MAN2A modulating agents are tested with an assay system comprising a MAN2A polypeptide or nucleic acid. Agents that produce a change in the activity of the assay system relative to controls are identified as candidate IGFR modulating agents. The assay system may be cell-based or cell-free. MAN2A-modulating agents include MAN2A related proteins (e.g. dominant negative mutants, and biotherapeutics); MAN2A-specific antibodies; MAN2A-specific antisense oligomers and other nucleic acid modulators; and chemical agents that specifically bind to or interact with MAN2A or compete with MAN2A binding partner (e.g. by binding to a MAN2A binding partner). In one specific embodiment, a small molecule modulator is identified using a hydrolase assay. In specific embodiments, the screening assay system is selected from a binding assay, an apoptosis assay, a cell proliferation assay, an angiogenesis assay, and a hypoxic induction assay.

In another embodiment, candidate IGFR pathway modulating agents are further tested using a second assay system that detects changes in the IGFR pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the IGFR pathway, such as an angiogenic, apoptotic, or cell proliferation disorder (e.g. cancer).

The invention further provides methods for modulating the MAN2A function and/or the IGFR pathway in a mammalian cell by contacting the mammalian cell with an agent that specifically binds a MAN2A polypeptide or nucleic acid. The agent may be a small molecule modulator, a nucleic acid modulator, or an antibody and may be administered to a mammalian animal predetermined to have a pathology associated with the IGFR pathway.

DETAILED DESCRIPTION OF THE INVENTION

A dominant loss of function screen was carried out in *Drosophila* to identify genes that interact with or modulate the IGFR signaling pathway. Modifiers of the IGFR pathway and their orthologs were identified. The CG4606 (Alpha-man-IIb) gene was identified as a modifier of the IGFR pathway. Accordingly, vertebrate orthologs of these modifiers, and preferably the human orthologs, MAN2A genes (i.e., nucleic acids and polypeptides) are attractive drug targets for the treatment of pathologies associated with a defective IGFR signaling pathway, such as cancer.

In vitro and in vivo methods of assessing MAN2A function are provided herein. Modulation of the MAN2A or their respective binding partners is useful for understanding the association of the IGFR pathway and its members in normal and disease conditions and for developing diagnostics and therapeutic modalities for IGFR related pathologies. MAN2A-modulating agents that act by inhibiting or enhancing MAN2A expression, directly or indirectly, for example, by affecting a MAN2A function such as enzymatic (e.g., catalytic) or binding activity, can be identified using methods provided herein. MAN2A modulating agents are useful in diagnosis, therapy and pharmaceutical development.

Nucleic Acids and Polypeptides of the Invention

Sequences related to MAN2A nucleic acids and polypeptides that can be used in the invention are disclosed in Genbank (referenced by Genbank identifier (GI) number) as GI#s 4758697 (SEQ ID NO:1), 1117826 (SEQ ID NO:2), 21734129 (SEQ ID NO:3), and 5540099 (SEQ ID NO:4) for nucleic acid, and GI#s 4758698 (SEQ ID NO:5) and 3123244 (SEQ ID NO:6) for polypeptide sequences.

The term "MAN2A polypeptide" refers to a full-length MAN2A protein or a functionally active fragment or derivative thereof. A "functionally active" MAN2A fragment or derivative exhibits one or more functional activities associated with a full-length, wild-type MAN2A protein, such as antigenic or immunogenic activity, enzymatic activity, ability to bind natural cellular substrates, etc. The functional activity of MAN2A proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active MAN2A polypeptide is a MAN2A derivative capable of rescuing defective endogenous MAN2A activity, such as in cell based or animal assays; the rescuing derivative may be from the same or a different species. For purposes herein, functionally active fragments also include those fragments that comprise one or more structural domains of a MAN2A, such as a binding domain. Protein domains can be identified using the PFAM program (Bateman A., et al., Nucleic Acids Res, 1999, 27:260-2). For example, the Glycosyl hydrolases family 38 N-terminus domain (PFAM 01074) of MAN2A from GIs# 4758698 and 3123244 (SEQ ID NOs:5 and 6, respectively) is located respectively at approximately amino acid residues 167 to 498 and 167 to 498. Also, the Glycosyl hydrolases family 38 C-terminus domain (PFAM 07748) of MAN2A from GIs# 4758698 and 3123244 (SEQ ID NOs:5 and 6, respectively) is located respectively at approximately amino acid residues 648 to 1139 and 648 to 1135. Methods for obtaining MAN2A polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a MAN2A. In further preferred embodiments, the fragment comprises the entire functionally active domain.

The term "MAN2A nucleic acid" refers to a DNA or RNA molecule that encodes a MAN2A polypeptide. Preferably, the MAN2A polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human MAN2A. Methods of identifying orthologs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10: 1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a MAN2A. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a MAN2A under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-expression of MAN2A Nucleic Acids and Polypeptides MAN2A nucleic acids and polypeptides are useful for identifying and testing agents that modulate MAN2A function and for other applications related to the involvement of MAN2A in the IGFR pathway. MAN2A nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a MAN2A protein for assays used to assess MAN2A function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant MAN2A is expressed in a cell line known to have defective IGFR function. The recombinant cells are used in cell-based screening assay systems of the invention, as described further below.

The nucleotide sequence encoding a MAN2A polypeptide can be inserted into any appropriate expression vector. The necessary transcriptional and translational signals, including promoter/enhancer element, can derive from the native MAN2A gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the MAN2A gene product, the expression vector can comprise a promoter operably linked to a MAN2A gene nucleic acid, one or more origins of replication, and, one or more selectable markers (e.g. thymidine kinase activity, resistance to antibiotics, etc.). Alternatively, recombinant expression vectors can be identified by assaying for the expression of the MAN2A gene product based on the physical or functional properties of the MAN2A protein in in vitro assay systems (e.g. immunoassays).

The MAN2A protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the MAN2A gene sequence is identified, the gene product can be isolated and purified using standard methods (e.g. ion exchange, affinity, and gel exclusion chromatography; centrifugation; differential solubility; electrophoresis). Alternatively, native MAN2A proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of MAN2A or other genes associated with the IGFR pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter MAN2A expression may be used in in vivo assays to test for activity of a candidate IGFR modulating agent, or to further assess the role of MAN2A in an IGFR pathway process such as apoptosis or cell proliferation. Preferably, the altered MAN2A expression results in a detectable phenotype, such as decreased or increased levels of cell proliferation, angiogenesis, or apoptosis compared to control animals having normal MAN2A expression. The genetically modified animal may additionally have altered IGFR expression (e.g. IGFR knockout). Preferred genetically modified animals are mammals such as primates, rodents (preferably mice or rats), among others. Preferred non-mammalian species include zebrafish, C. elegans, and Drosophila. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic Drosophila see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous MAN2A gene that results in a decrease of MAN2A function, preferably such that MAN2A expression is undetectable or insignificant. Knockout animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse MAN2A gene is used to construct a homologous recombination vector suitable for altering an endogenous MAN2A gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the MAN2A gene, e.g., by introduction of additional copies of MAN2A, or by operatively inserting a regulatory sequence that provides for altered expression of an endogenous copy of the MAN2A gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat.

No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the IGFR pathway, as animal models of disease and disorders implicating defective IGFR function, and for in vivo testing of candidate therapeutic agents, such as those identified in screens described below. The candidate therapeutic agents are administered to a genetically modified animal having altered MAN2A function and phenotypic changes are compared with appropriate control animals such as genetically modified animals that receive placebo treatment, and/or animals with unaltered MAN2A expression that receive candidate therapeutic agent.

In addition to the above-described genetically modified animals having altered MAN2A function, animal models having defective IGFR function (and otherwise normal MAN2A function), can be used in the methods of the present invention. For example, an IGFR knockout mouse can be used to assess, in vivo, the activity of a candidate IGFR modulating agent identified in one of the in vitro assays described below. Preferably, the candidate IGFR modulating agent when administered to a model system with cells defective in IGFR function, produces a detectable phenotypic change in the model system indicating that the IGFR function is restored, i.e., the cells exhibit normal cell cycle progression.

Modulating Agents

The invention provides methods to identify agents that interact with and/or modulate the function of MAN2A and/or the IGFR pathway. Modulating agents identified by the methods are also part of the invention. Such agents are useful in a variety of diagnostic and therapeutic applications associated with the IGFR pathway, as well as in further analysis of the MAN2A protein and its contribution to the IGFR pathway. Accordingly, the invention also provides methods for modulating the IGFR pathway comprising the step of specifically modulating MAN2A activity by administering a MAN2A-interacting or -modulating agent.

As used herein, a "MAN2A-modulating agent" is any agent that modulates MAN2A function, for example, an agent that interacts with MAN2A to inhibit or enhance MAN2A activity or otherwise affect normal MAN2A function. MAN2A function can be affected at any level, including transcription, protein expression, protein localization, and cellular or extra-cellular activity. In a preferred embodiment, the MAN2A-modulating agent specifically modulates the function of the MAN2A. The phrases "specific modulating agent", "specifically modulates", etc., are used herein to refer to modulating agents that directly bind to the MAN2A polypeptide or nucleic acid, and preferably inhibit, enhance, or otherwise alter, the function of the MAN2A. These phrases also encompass modulating agents that alter the interaction of the MAN2A with a binding partner, substrate, or cofactor (e.g. by binding to a binding partner of a MAN2A, or to a protein/binding partner complex, and altering MAN2A function). In a further preferred embodiment, the MAN2A-modulating agent is a modulator of the IGFR pathway (e.g. it restores and/or upregulates IGFR function) and thus is also an IGFR-modulating agent.

Preferred MAN2A-modulating agents include small molecule compounds; MAN2A-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the MAN2A protein or may be identified by screening compound libraries. Alternative appropriate modulators of this class are natural products, particularly secondary metabolites from organisms such as plants or fungi, which can also be identified by screening compound libraries for MAN2A-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the IGFR pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific MAN2A-interacting proteins are useful in a variety of diagnostic and therapeutic applications related to the IGFR pathway and related disorders, as well as in validation assays for other MAN2A-modulating agents. In a preferred embodiment, MAN2A-interacting proteins affect normal MAN2A function, including transcription, protein expression, protein localization, and cellular or extra-cellular activity. In another embodiment, MAN2A-interacting proteins are useful in detecting and providing information about the function of MAN2A proteins, as is relevant to IGFR related disorders, such as cancer (e.g., for diagnostic means).

A MAN2A-interacting protein may be endogenous, i.e. one that naturally interacts genetically or biochemically with a MAN2A, such as a member of the MAN2A pathway that modulates MAN2A expression, localization, and/or activity.

MAN2A-modulators include dominant negative forms of MAN2A-interacting proteins and of MAN2A proteins themselves. Yeast two-hybrid and variant screens offer preferred methods for identifying endogenous MAN2A-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928, 868). Mass spectrometry is an alternative preferred method for the elucidation of protein complexes (reviewed in, e.g., Pandley A and Mann M, Nature (2000) 405:837-846; Yates J R 3rd, Trends Genet (2000) 16:5-8).

An MAN2A-interacting protein may be an exogenous protein, such as a MAN2A-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). MAN2A antibodies are further discussed below.

In preferred embodiments, a MAN2A-interacting protein specifically binds a MAN2A protein. In alternative preferred embodiments, a MAN2A-modulating agent binds a MAN2A substrate, binding partner, or cofactor.

Antibodies

In another embodiment, the protein modulator is a MAN2A specific antibody agonist or antagonist. The antibodies have therapeutic and diagnostic utilities, and can be used in screening assays to identify MAN2A modulators. The antibodies can also be used in dissecting the portions of the MAN2A pathway responsible for various cellular responses and in the general processing and maturation of the MAN2A.

Antibodies that specifically bind MAN2A polypeptides can be generated using known methods. Preferably the antibody is specific to a mammalian ortholog of MAN2A polypeptide, and more preferably, to human MAN2A. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of MAN2A which are particularly antigenic can be selected, for example, by routine screening of MAN2A polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence of a MAN2A. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451, 570; and 4,618,577). Antibodies may be generated against crude cell extracts of MAN2A or substantially purified fragments thereof. If MAN2A fragments are used, they preferably comprise at least 10, and more preferably, at least 20 contiguous amino acids of a MAN2A protein. In a particular embodiment, MAN2A-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of MAN2A-specific antibodies is assayed by an appropriate assay such as a solid phase enzyme-linked immunosorbant assay (ELISA) using immobilized corresponding MAN2A polypeptides. Other assays, such as radioimmunoassays or fluorescent assays might also be used.

Chimeric antibodies specific to MAN2A polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co MS, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

MAN2A-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Specific Biotherapeutics

In a preferred embodiment, a MAN2A-interacting protein may have biotherapeutic applications. Biotherapeutic agents formulated in pharmaceutically acceptable carriers and dosages may be used to activate or inhibit signal transduction pathways. This modulation may be accomplished by binding a ligand, thus inhibiting the activity of the pathway; or by binding a receptor, either to inhibit activation of, or to activate, the receptor. Alternatively, the biotherapeutic may itself be a ligand capable of activating or inhibiting a receptor. Biotherapeutic agents and methods of producing them are described in detail in U.S. Pat. No. 6,146,628.

When the MAN2A is a ligand, it may be used as a biotherapeutic agent to activate or inhibit its natural receptor. Alternatively, antibodies against MAN2A, as described in the previous section, may be used as biotherapeutic agents.

When the MAN2A is a receptor, its ligand(s), antibodies to the ligand(s) or the MAN2A itself may be used as biotherapeutics to modulate the activity of MAN2A in the IGFR pathway.

Nucleic Acid Modulators

Other preferred MAN2A-modulating agents comprise nucleic acid molecules, such as antisense oligomers or double stranded RNA (dsRNA), which generally inhibit MAN2A activity. Preferred nucleic acid modulators interfere with the function of the MAN2A nucleic acid such as DNA replication, transcription, translocation of the MAN2A RNA to the site of protein translation, translation of protein from the MAN2A RNA, splicing of the MAN2A RNA to yield one or more mRNA species, or catalytic activity which may be engaged in or facilitated by the MAN2A RNA.

In one embodiment, the antisense oligomer is an oligonucleotide that is sufficiently complementary to a MAN2A mRNA to bind to and prevent translation, preferably by binding to the 5' untranslated region. MAN2A-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred MAN2A nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498; Novina C D and Sharp P. 2004 Nature 430:161-164; Soutschek J et al 2004 Nature 432:173-178).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a MAN2A-specific nucleic acid modulator is used in an assay to further elucidate the role of the MAN2A in the IGFR pathway, and/or its relationship to other members of the pathway. In another aspect of the invention, a MAN2A-specific antisense oligomer is used as a therapeutic agent for treatment of IGFR-related disease states.

Assay Systems

The invention provides assay systems and screening methods for identifying specific modulators of MAN2A activity. As used herein, an "assay system" encompasses all the components required for performing and analyzing results of an assay that detects and/or measures a particular event. In general, primary assays are used to identify or confirm a modulator's specific biochemical or molecular effect with respect to the MAN2A nucleic acid or protein. In general, secondary assays further assess the activity of a MAN2A modulating agent identified by a primary assay and may confirm that the modulating agent affects MAN2A in a manner relevant to the IGFR pathway. In some cases, MAN2A modulators will be directly tested in a secondary assay.

In a preferred embodiment, the screening method comprises contacting a suitable assay system comprising a MAN2A polypeptide or nucleic acid with a candidate agent under conditions whereby, but for the presence of the agent, the system provides a reference activity (e.g. hydrolase activity), which is based on the particular molecular event the screening method detects. A statistically significant difference between the agent-biased activity and the reference activity indicates that the candidate agent modulates MAN2A activity, and hence the IGFR pathway. The MAN2A polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of MAN2A and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when MAN2A-interacting proteins are used in screens to identify small molecule modulators, the binding specificity of the interacting protein to the MAN2A protein may be assayed by various known methods such as substrate processing (e.g. ability of the candidate MAN2A-specific binding agents to function as negative effectors in MAN2A-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit MAN2A specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a MAN2A polypeptide, a fusion protein thereof, or to cells or membranes bearing the polypeptide or fusion protein. The MAN2A polypeptide can be full length or a fragment thereof that retains functional MAN2A activity. The MAN2A polypeptide may be fused to another polypeptide, such as a peptide tag for detection or anchoring, or to another tag. The MAN2A polypeptide is preferably human MAN2A, or is an ortholog or derivative thereof as described above. In a preferred embodiment, the screening assay detects candidate agent-based modulation of MAN2A interaction with a binding target, such as an endogenous or exogenous protein or other substrate that has MAN2A-specific binding activity, and can be used to assess normal MAN2A gene function.

Suitable assay formats that may be adapted to screen for MAN2A modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate MAN2A and IGFR pathway modulators (e.g. U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

Hydrolase assays. Hydrolases catalyze the hydrolysis of a substrate such as esterases, lipases, peptidases, nucleotidases, and phosphatases, among others. Enzyme activity assays may be used to measure hydrolase activity. The activity of the enzyme is determined in presence of excess substrate, by spectrophotometrically measuring the rate of appearance of reaction products. High throughput arrays and assays for hydrolases are known to those skilled in the art (Park C B and Clark D S (2002) Biotech Bioeng 78:229-235).

Apoptosis assays. Apoptosis or programmed cell death is a suicide program is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™ Homogeneous Caspase-3/7 assay from Promega, cat# 67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat# 1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumalation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phosphohistone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as Cellomics™ ArrayScan® HCS System. The measurable parameters and their markers include antiactive caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, TOTO-3 fluorescent dye which labels DNA of dead cells with high cell membrane permeability, and anti-alpha-tubulin or F-actin labels, which assess cytoskeletal changes in cells and correlate well with TOTO-3 label.

An apoptosis assay system may comprise a cell that expresses a MAN2A, and that optionally has defective IGFR function (e.g. IGFR is over-expressed or under-expressed relative to wild-type cells). A test agent can be added to the apoptosis assay system and changes in induction of apoptosis relative to controls where no test agent is added, identify candidate IGFR modulating agents. In some embodiments of the invention, an apoptosis assay may be used as a secondary assay to test a candidate IGFR modulating agents that is initially identified using a cell-free assay system. An apoptosis assay may also be used to test whether MAN2A function plays a direct role in apoptosis. For example, an apoptosis assay may be performed on cells that over- or under-express MAN2A relative to wild type cells. Differences in apoptotic response compared to wild type cells suggests that the MAN2A plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specfic to the phosphorylated form of the serine 10 residue of histone H3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 96® AQueous Non-Radioactive Cell Proliferation Assay (Cat.# G5421).

Cell proliferation may also be assayed by colony formation in soft agar, or clonogenic survival assay (Sambrook et al., Molecular Cloning, Cold Spring Harbor (1989)). For example, cells transformed with MAN2A are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a MAN2A may be stained with propidium iodide and evaluated in a flow cytometer (available from Becton Dickinson), which indicates accumulation of cells in different stages of the cell cycle.

Involvement of a gene in cell cycle may also be assayed by FOXO nuclear translocation assays. The FOXO family of transcription factors are mediators of various cellular functions including cell cycle progression and cell death, and are negatively regulated by activation of the PI3 kinase pathway. Akt phosphorylation of FOXO family members leads to FOXO sequestration in the cytoplasm and transcriptional inactivation (Medema, R. H et al (2000) Nature 404: 782-787). PTEN is a negative regulator of PI3 kinase pathway. Activation of PTEN, or loss of PI3 kinase or AKT, prevents phosphorylation of FOXO, leading to accumulation of FOXO in the nucleus, transcriptional activation of FOXO regulated genes, and apoptosis. Alternatively, loss of PTEN leads to pathway activation and cell survival (Nakamura, N. et al (2000) Mol Cell Biol 20: 8969-8982). FOXO translocation into the cytoplasm is used in assays and screens to identify members and/or modulators of the PTEN pathway. FOXO translocation assays using GFP or luciferase as detection reagents are known in the art (e.g., Zhang X et al (2002) J Biol Chem 277:45276-45284; and Li et al (2003) Mol Cell Biol 23:104-118).

Accordingly, a cell proliferation or cell cycle assay system may comprise a cell that expresses a MAN2A, and that optionally has defective IGFR function (e.g. IGFR is overexpressed or under-expressed relative to wild-type cells). A test agent can be added to the assay system and changes in cell proliferation or cell cycle relative to controls where no test agent is added, identify candidate IGFR modulating agents. In some embodiments of the invention, the cell proliferation or cell cycle assay may be used as a secondary assay to test a candidate IGFR modulating agents that is initially identified using another assay system such as a cell-free assay system. A cell proliferation assay may also be used to test whether MAN2A function plays a direct role in cell proliferation or cell cycle. For example, a cell proliferation or cell cycle assay may be performed on cells that over- or under-express MAN2A relative to wild type cells. Differences in proliferation or cell cycle compared to wild type cells suggests that the MAN2A plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HIS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a MAN2A, and that optionally has defective IGFR function (e.g. IGFR is over-expressed or under-expressed relative to wild-type cells). A test agent can be added to the angiogenesis assay system and changes in angiogenesis relative to controls where no test agent is added, identify candidate IGFR modulating agents. In some embodiments of the invention, the angiogenesis assay may be used as a secondary assay to test a candidate IGFR modulating agents that is initially identified using another assay system. An angiogenesis assay may also be used to test whether MAN2A function plays a direct role in cell proliferation. For example, an angiogenesis assay may be performed on cells that over- or under-express MAN2A relative to wild type cells. Differences in angiogenesis compared to wild type cells suggests that the MAN2A plays a direct role in angiogenesis. U.S. Pat. Nos. 5,976,782, 6,225,118 and 6,444,434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with MAN2A in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a MAN2A, and that optionally has defective IGFR function (e.g. IGFR is over-expressed or under-expressed relative to wild-type cells). A test agent can be added to the hypoxic induction assay system and changes in hypoxic response relative to controls where no test agent is added, identify candidate IGFR modulating agents. In some embodiments of the invention, the hypoxic induction assay may be used as a secondary assay to test a candidate IGFR modulating agents that is initially identified using another assay system. A hypoxic induction assay may also be used to test whether MAN2A function plays a direct role in the hypoxic response. For example, a hypoxic induction assay may be performed on cells that over- or under-express MAN2A relative to wild type cells. Differences in hypoxic response compared to wild type cells suggests that the MAN2A plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the MAN2A protein. Methods for testing antibody affinity and specificity are well known in the art (Harlow and Lane, 1988, 1999, supra). The enzyme-linked immunosorbant assay (ELISA) is a preferred method for detecting MAN2A-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance MAN2A gene expression, preferably mRNA expression. In general, expression analysis comprises comparing MAN2A expression in like populations of cells (e.g., two pools of cells that endogenously or recombinantly express MAN2A) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that MAN2A mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the MAN2A protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve MAN2A mRNA expression, may also be used to test nucleic acid modulators.

Secondary Assays

Secondary assays may be used to further assess the activity of MAN2A-modulating agent identified by any of the above methods to confirm that the modulating agent affects MAN2A in a manner relevant to the IGFR pathway. As used herein, MAN2A-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with MAN2A.

Secondary assays generally compare like populations of cells or animals (e.g., two pools of cells or animals that endogenously or recombinantly express MAN2A) in the presence and absence of the candidate modulator. In general, such assays test whether treatment of cells or animals with a candidate MAN2A-modulating agent results in changes in the IGFR pathway in comparison to untreated (or mock- or placebo-treated) cells or animals. Certain assays use "sensitized genetic backgrounds", which, as used herein, describe cells or animals engineered for altered expression of genes in the IGFR or interacting pathways.

Cell-based Assays

Cell based assays may detect endogenous IGFR pathway activity or may rely on recombinant expression of IGFR pathway components. Any of the aforementioned assays may be used in this cell-based format. Candidate modulators are typically added to the cell media but may also be injected into cells or delivered by any other efficacious means.

Animal Assays

A variety of non-human animal models of normal or defective IGFR pathway may be used to test candidate MAN2A modulators. Models for defective IGFR pathway typically use genetically modified animals that have been engineered to mis-express (e.g., over-express or lack expression in) genes involved in the IGFR pathway. Assays generally require systemic delivery of the candidate modulators, such as by oral administration, injection, etc.

In a preferred embodiment, IGFR pathway activity is assessed by monitoring neovascularization and angiogenesis. Animal models with defective and normal IGFR are used to test the candidate modulator's affect on MAN2A in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which overexpress the MAN2A. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on MAN2A is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the MAN2A endogenously are injected in the flank, $1\times10^5$ to $1\times10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific MAN2A-modulating agents are useful in a variety of diagnostic and therapeutic applications where disease or disease prognosis is related to defects in the IGFR pathway, such as angiogenic, apoptotic, or cell proliferation disorders. Accordingly, the invention also provides methods for modulating the IGFR pathway in a cell, preferably a cell predetermined to have defective or impaired IGFR function (e.g. due to overexpression, underexpression, or misexpression of IGFR, or due to gene mutations), comprising the step of administering an agent to the cell that specifically modulates MAN2A activity. Preferably, the modulating agent produces a detectable phenotypic change in the cell indicating that the IGFR function is restored. The phrase "function is restored", and equivalents, as used herein, means that the desired phenotype is achieved, or is brought closer to normal compared to untreated cells. For example, with restored IGFR function, cell proliferation and/or progression through cell cycle may normalize, or be brought closer to normal relative to untreated cells. The invention also provides methods for treating disorders or disease associated with impaired IGFR function by administering a therapeutically effective amount of a MAN2A-modulating agent that modulates the IGFR pathway. The invention further provides methods for modulating MAN2A function in a cell, preferably a cell pre-determined to have defective or impaired MAN2A function, by administering a MAN2A-modulating agent. Additionally, the invention provides a method for treating disorders or disease associated with impaired MAN2A function by administering a therapeutically effective amount of a MAN2A-modulating agent.

The discovery that MAN2A is implicated in IGFR pathway provides for a variety of methods that can be employed for the diagnostic and prognostic evaluation of diseases and disorders involving defects in the IGFR pathway and for the identification of subjects having a predisposition to such diseases and disorders.

Various expression analysis methods can be used to diagnose whether MAN2A expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective IGFR signaling that express a MAN2A, are identified as amenable to treatment with a MAN2A modulating agent. In a preferred application, the IGFR defective tissue overexpresses a MAN2A relative to normal tissue. For example, a Northern blot analysis of mRNA from tumor and normal cell lines, or from tumor and matching normal tissue samples from the same patient, using full or partial MAN2A cDNA sequences as probes, can determine whether particular tumors express or overexpress MAN2A. Alternatively, the TaqMan® is used for quantitative RT-PCR analysis of MAN2A expression in cell lines, normal tissues and tumor samples (PE Applied Biosystems).

Various other diagnostic methods may be performed, for example, utilizing reagents such as the MAN2A oligonucleotides, and antibodies directed against a MAN2A, as described above for: (1) the detection of the presence of MAN2A gene mutations, or the detection of either over- or under-expression of MAN2A mRNA relative to the non-disorder state; (2) the detection of either an over- or an under-abundance of MAN2A gene product relative to the non-disorder state; and (3) the detection of perturbations or abnormalities in the signal transduction pathway mediated by MAN2A.

Kits for detecting expression of MAN2A in various samples, comprising at least one antibody specific to MAN2A, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in MAN2A expression, the method comprising: a) obtaining a biological sample from the patient; b) contacting the sample with a probe for MAN2A expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* IGFR Overexpression Screen

A dominant loss of function screen was carried out in *Drosophila* to identify genes that interact with or modulate the IGFR signaling pathway. Activation of the pathway by overexpression of IGFR at early stages in the developing *Drosophila* eye leads to an increase in cell number which results in a larger and rougher adult eye (Potter C J et al. (2001) Cell 105:357-368; Huang et al., 1999. Dev. 126:5365-5372). We generated a fly stock with an enlarged eye due to overexpression of IGFR and identified modifiers of this phenotype. We then identified human orthologues of these modifiers.

The screening stock carried two transgenes. The genotype is as follows:

+; +; P{DmIGFR-pExp-UAS)} P{Gal4-pExp-1Xey}/TM6B

Screening stock females of the above genotype were crossed to males from a collection of 3 classes of piggyBac-based transposons. The resulting progeny, which contain both the transgenes and the transposon, were scored for the effect of the transposon on the eye overgrowth phenotype (either enhancement, suppression or no effect). All data was recorded and all modifiers were retested with a repeat of the original cross. Modifiers of the eye phenotype were identified as members of the IGFR pathway. CG4606 (Alpha-man-IIb) was a suppressor of the eye phenotype. Orthologs of the modifiers are referred to herein as MAN2A.

BLAST analysis (Altschul et al., supra) was employed to identify orthologs of *Drosophila* modifiers. For example, representative sequences from MAN2A, GI# 4758698 (SEQ ID NO:5), and GI#3123244 (SEQ ID NO:6) share 43% and 44% amino acid identity, respectively, with the *Drosophila* CG4606 (Alpha-man-IIb).

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the *Caenorhabditis elegans* genome and identification of human orthologs. Genome Res. 2000 November; 10(11): 1679-89) programs. For example, the Glycosyl hydrolases family 38 N-terminus domain (PFAM 01074) of MAN2A from GIs# 4758698 and 3123244 (SEQ ID NOs:5 and 6, respectively) is located respectively at approximately amino acid residues 167 to 498 and 167 to 498. Also, the Glycosyl hydrolases family 38 C-terminus domain (PFAM 07748) of MAN2A from GIs# 4758698 and 3123244 (SEQ ID NOs:5 and 6, respectively) is located respectively at approximately amino acid residues 648 to 1139 and 648 to 1135.

II. High-Throughput In Vitro Fluorescence Polarization Assay

Fluorescently-labeled MAN2A peptide/substrate are added to each well of a 96-well microtiter plate, along with a test agent in a test buffer (10 mM BEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of MAN2A activity.

III. High-Throughput In Vitro Binding Assay.

$^{33}$P-labeled MAN2A peptide is added in an assay buffer (100 mM KCl, 20 mM HEPES pH 7.6, 1 mM MgCl2, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate IGFR modulating agents.

IV. Immunoprecipitations and Immunoblotting

For coprecipitation of transfected proteins, $3 \times 10^6$ appropriate recombinant cells containing the MAN2A proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, Clontech, Stratagene, Ardais, Genome Collaborative, and Ambion.

TaqMan® analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 430-4965 of Applied Biosystems (Foster City, Calif.).

Primers for expression analysis using TaqMan® assay (Applied Biosystems, Foster City, Calif.) were prepared according to the TaqMan® protocols, and the following criteria: a) primer pairs were designed to span introns to eliminate genomic contamination, and b) each primer pair produced only one product. Expression analysis was performed using a 7900HT instrument.

TaqMan® reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor-average (all normal samples)>2× STDEV (all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| Gene Name | MAN2A1 SEQ ID NO:1) | MAN2A2 (SEQ ID NO:4) |
|---|---|---|
| Breast | 17% | 8% |
| # of Pairs | 36 | 36 |
| Colon | 12% | 8% |
| # of Pairs | 40 | 40 |
| Head And Neck | 8% | 0% |
| # of Pairs | 13 | 13 |

TABLE 1-continued

| Gene Name | MAN2A1 SEQ ID NO:1) | MAN2A2 (SEQ ID NO:4) |
|---|---|---|
| Liver | 11% | 22% |
| # of Pairs | 9 | 9 |
| Lung | 10% | 2% |
| # of Pairs | 40 | 40 |
| Lymphoma | 0% | 0% |
| # of Pairs | 4 | 4 |
| Ovary | 5% | 21% |
| # of Pairs | 19 | 19 |
| Pancreas | 42% | 33% |
| # of Pairs | 12 | 12 |
| Prostate | 8% | 8% |
| # of Pairs | 24 | 24 |
| Skin | 0% | 43% |
| # of Pairs | 7 | 7 |
| Stomach | 0% | 9% |
| # of Pairs | 11 | 11 |
| Testis | 0% | 0% |
| # of Pairs | 8 | 8 |
| Thyroid Gland | 14% | 7% |
| # of Pairs | 14 | 14 |
| Uterus | 17% | 9% |
| # of Pairs | 23 | 23 |

VI. MAN2A Functional Assays

RNAi experiments were carried out to knock down expression of MAN2A1 and MAN2A2 (SEQ ID NOs: 1 and 4, respectively) in various cell lines using small interfering RNAs (siRNA, Elbashir et al, supra).

Effect of MAN2A RNAi on cell proliferation and growth. BrdU and Cell Titer-Glo™ assays, as described above, were employed to study the effects of decreased MAN2A expression on cell proliferation. The results of these experiments indicated that RNAi of both MAN2A1 and MAN2A2 (SEQ ID Nos: 1 and 4) decreased proliferation in 231T breast cancer cells, A549 lung cancer cells, PC3 prostate cancer cells, and U87MG glioblastoma cells.

Standard colony growth assays, as described above, were employed to study the effects of decreased MAN2A expression on cell growth. The results of this experiment indicated that RNAi of MAN2A1 (SEQ ID NO: 1) decreased proliferation in A549 cells and A2780 ovarian cancer cells, while causing decreased cell count in 231T, PC3, and A549 cells. RNAi of MAN2A2 (SEQ ID NO:4) caused decreased cell count in A549 cells.

[$^3$H]-thymidine incorporation assay, as described above, was also employed to study the effects of decreased MAN2A expression on cell proliferation. The results of this experiment indicated that RNAi of MAN2A of SEQ ID NO:1 decreased proliferation in A549 and A2780 cells, and also in RD1 rhabdomyosarcoma cells. RNAi of MAN2A of SEQ ID NO:4 decreased proliferation in A549 and RD1 cells.

Effect of MAN2A RNAi on apoptosis. The Phospho-histone H2B assay, as described above, was employed to study the effects of decreased MAN2A expression on apoptosis. The results of this experiment indicated that RNAi of MAN2A of SEQ ID NO:1 increased apoptosis in 23 iT, PC3, and U87MG cells; and RNAi of MAN2A of SEQ ID NO:4 increased apoptosis in PC3 cells.

Multiple paramater apoptosis assay, as described above, was also used to study the effects of decreased MAN2A expression on apoptosis. The results of this experiment indicated that RNAi of each MAN2A1 and MAN2A2 (SEQ ID Nos:1 and 4) increased apoptosis in A2780 and A549 cells.

Transcriptional reporter assays. Effects of overexpressed MAN2A on expression of various transcription factors was also studied. Overexpressed MAN2A caused an increased expression of the following transcription factors: ??????. Additionally, other transcriptional reporter assay was also performed to measure the effects of overexpressed MAN2A on expression of various transcription factors. In this assay, rat intestinal epithelial cells (RIEs) or NIH3T3 cells were co-transfected with reporter constructs containing various transcription factors and luciferase along with MAN2A. Luciferase intensity was then measured as the readout for transcriptional activation due to overexpression of the MAN2A. Overexpressed MAN2A of SEQ ID NO:1 caused an increased expression of API (Activator protein 1) transcription factor.

Involvement in PTEN/IGF pathway: MAN2A FOXO nuclear translocation assays. FOXO nuclear translocation assays, as described above, were employed to assess involvement of MAN2A in the PTEN/IGF pathway. In one set of experiments, cells with reduced expression of MAN2A by RNAi were transiently transfected with a plasmid expressing GFP-tagged FOXO. Automated imaging of cellular components, such as nucleus and cytoplasm were then carried out to assess translocation of FOXO. Results indicated that reduced expression of MAN2A of SEQ ID NO:1 led to retention of FOXO in the nucleus, translocation of FOXO to the cytoplasm, similar to loss of PTEN, in U20S osteosarcoma cells. In another set of experiments, cells were co-transfected with siRNA directed to MAN2A along with a plasmid containing FOXO, and a cassette containing a promoter, a FOXO response element, and luciferase. Cells were then analyzed for luciferase activity and compared with cells with no siRNA. Results indicated that reduced expression of MAN2A1 (SEQ ID NO:1) led to translocation of FOXO to the cytoplasm in A2780 and PC3 cells, and reduced expression of MAN2A2 (SEQ ID NO:4) led to translocation of FOXO to the cytoplasm in A2780 cells. These results suggest involvement of MAN2A in the PTEN/IGFR pathway.

Pan-AKT assays. This assay was developed to detect involvement of MAN2A in the PTEN/IGFR pathway. The assay detects changes in phosphorylation for several substrates of AKT, such as PRAS40, BAD, 4EBP1, and RPS6. For this experiment, antibodies were raised against phosphorylated AKT substrates, including the consensus phosphorylated AKT substrate sequence RxRxxS/T. Expression levels of phosphorylated substrates were then quantitated at normal levels, in presence of a negative control, a positive control (AKT), and then with MAN2A knockout. For example, when AKT levels were reduced, expression of all its substrates was also reduced. Results indicated that RNAi of MAN2A1 and MAN2A2 (SEQ ID NOs:1 and 4, respectively), reduced the level of phosphorylated AKT substrates in 231T and A549 cells.

We used RPS6 as a substrate for one subset of experiments. RPS6 is an IGF dependent substrate of AKT. IGF1 treatment increases cytoplasmic RPS6 levels. Alternatively, Lily compound LY294002, a PI3K inhibitor, reduces AKT and cytoplasmic RPS6 levels. Cells were plated in 96 well plates, transfected with RNAi for MAN2A, fixed, treated with RPS6 antibody, and stained. Measurements were based on percentage of population of cells with increased or decreased staining compared with negative or positive control cells. Results of this experiment showed that RNAi of MAN2A1 (SEQ ID NO: 1) caused a reduction in the amount of phosphorylated RPS6 in A549 cells.

We used 4EBP1 as the substrate in another subset of experiments. For this substrate, AKT pathway inhibition causes decreased cytoplasmic staining and increased nuclear staining. Cells were plated in 96 well plates, transfected with RNAi for MAN2A, fixed, treated with 4EBP1 antibody, and stained. Measurements were based on percentage of population of cells with increased or decreased nuclear/cytoplasmic staining ratio compared with negative or positive control cells. Results of this experiment showed that RNAi of MAN2A1 (SEQ ID NO:1) caused a reduction in the amount of phosphorylated 4EBP1 in A549 cells.

We also used PRAS40 as the substrate another subset of experiments. For this substrate, pathway inhibition causes decreased cytoplasmic staining and increased nuclear and perinuclear staining. Cells were plated in 96 well plates, transfected with RNAi for MAN2A, fixed, treated with PRAS40 antibody, and stained. Measurements were based on percentage of population of cells with increased or decreased nuclear/cytoplasmic staining ratio compared with negative or positive control cells. Results of this experiment showed that RNAi of MAN2A1 (SEQ ID NO:1) caused a reduction in the amount of phosphorylated PRAS40 in 23 IT, PC3, and A549 cells; and RNAi of MAN2A2 (SEQ ID NO:4) caused a reduction in the amount of phosphorylated PRAS40 in A549 cells. Taken together, these results suggest involvement of MAN2A in the IGFR pathway.

High Throughput PTEN/IGF Transcriptional readout assay. This assay is an expanded TaqMan® transcriptional readout assay monitoring changes in the mRNA levels of endogenous PTEN/IGF regulated genes. This assay measures changes in expression of PTEN/IGF regulated cellular genes as a readout for pathway signaling activity.

We identified a panel of genes that were transcriptionally regulated by PTEN/IGF signaling, then designed and tested TaqMan® primer/probes sets. We reduced expression of PTEN/IGF by RNAi, and tested its affect on the expression of the transcriptionally regulated genes in multiple cell types. The panel readout was then narrowed to the ten most robust probes.

We then treated cancer cells with siRNAs of the target genes of interest, such as MAN2A, and tested how the reduced levels of the target genes affected the expression levels of the PTEN/IGF regulated gene panel.

Genes that when knocked out via at least 2 different RNAi oligos, demonstrated the same pattern of activity on at least one third of the panel genes as a PTEN/IGF knockout, were identified as involved in the PTEN/IGF pathway.

TaqMan® assays were performed on the RNAs in a 384 well format.

RNAi of MAN2A1 (SEQ ID NO: 1) showed the same pattern of activity as PTEN/IGF RNAi for at least 2 RNAi oligos on at least one third of the transcriptionally regulated genes in 231T and PC3 cells.

What is claimed is:

1. A method of identifying a candidate IGFR pathway modulating agent, said method comprising the steps of:
   (a) providing an assay system comprising a MAN2A polypeptide or nucleic acid;
   (b) contacting the assay system with a test agent under conditions whereby, but for the presence of the test agent, the system provides a reference activity; and
   (c) detecting a test agent-biased activity of the assay system, wherein a difference between the test agent-biased activity and the reference activity identifies the test agent as a candidate IGFR pathway modulating agent.

2. The method of claim 1 wherein the assay system comprises cultured cells that express the MAN2A polypeptide.

3. The method of claim 2 wherein the cultured cells additionally have defective IGFR function.

4. The method of claim 1 wherein the assay system includes a screening assay comprising a MAN2A polypeptide, and the candidate test agent is a small molecule modulator.

5. The method of claim 4 wherein the assay is a hydrolase assay.

6. The method of claim 1 wherein the assay system is selected from the group consisting of an apoptosis assay system, a cell proliferation assay system, an angiogenesis assay system, and a hypoxic induction assay system.

7. The method of claim 1 wherein the assay system includes a binding assay comprising a MAN2A polypeptide and the candidate test agent is an antibody.

8. The method of claim 1 wherein the assay system includes an expression assay comprising a MAN2A nucleic acid and the candidate test agent is a nucleic acid modulator.

9. The method of claim 8 wherein the nucleic acid modulator is an antisense oligomer.

10. The method of claim 8 wherein the nucleic acid modulator is a PMO.

11. The method of claim 1 additionally comprising:
(d) administering the candidate IGFR pathway modulating agent identified in (c) to a model system comprising cells defective in IGFR function and, detecting a phenotypic change in the model system that indicates that the IGFR function is restored.

12. The method of claim 11 wherein the model system is a mouse model with defective IGFR function.

13. The method of claim 1, comprising the additional steps of:
(d) providing a secondary assay system comprising cultured cells or a non-human animal expressing MAN2A,
(e) contacting the secondary assay system with the test agent of (b) or an agent derived therefrom under conditions whereby, but for the presence of the test agent or agent derived therefrom, the system provides a reference activity; and
(f) detecting an agent-biased activity of the second assay system,
wherein a difference between the agent-biased activity and the reference activity of the second assay system confirms the test agent or agent derived therefrom as a candidate IGFR pathway modulating agent,
and wherein the second assay detects an agent-biased change in the IGFR pathway.

14. The method of claim 13 wherein the secondary assay system comprises cultured cells.

15. The method of claim 13 wherein the secondary assay system comprises a non-human animal.

16. The method of claim 15 wherein the non-human animal mis-expresses an IGFR pathway gene.

* * * * *

SEQUENCE LISTING

```
<160> NUMBER OF SEQ ID NOS: 6

<210> SEQ ID NO 1
<211> LENGTH: 4101
<212> TYPE: DNA
<213> ORGANISM: Homo sapiens

<400> SEQUENCE: 1
ggctcctcgc gatcttgttc ctttccctc cgcttctctg acctagctgc gcggccccgg      60
cccgggagct gccgaacccg cgcctcccct gggtgaggag gacacgcctg ccctcgtcga     120 gaaaacttt  cctgccgact cagttggggc ggcggtggca ggaagtgcgg gcagcgacct     180
ctcctccgcc tgccccgcgc gccctgccgg aggtcggcgc tgagcttgcg atcaagtttg     240
tgggggcccc ccttcccagt tgccggcgag tctcgcctcg agagggcgc ccgacccgg      300 ggagggcggc aggccagggc gaaggccaag ggcgttttgt ggcgccggag actaggtgcg     360
gagcaaggcg gggactcgca cccgcatccg agagcgcgga ggtcgcgcag cccgggagaa     420
gggagcctcc ggcggctgct tcctagagtc cacagtgcgc tgtctccttt ggctgaggag     480
agtgtcctgg ccccgagtct atcgaggaaa atgaagttaa gccgccagtt caccgtgttc     540
ggcagtgcga tcttctgtgt ggtgatttc tcgctctacc tgatgctgga ccggggtcac     600
ttagactacc ccaggaaccc gcgccgcgag ggctccttcc ctcagggcca gctctcaatg     660
ttgcaagaaa aaatagacca tttggagcgt ttgctagctg agaataatga gatcatctca     720 aatattgag  actcagtcat caatttgagt gagtctgtgg aggatggtcc gaaaagttca     780
caaagcaatt tcagccaagg tgctggctca catcttctgc cctcacaatt atccctctca     840
gttgacactg cagactgtct gtttgcttca caaagtggaa gtcacaattc agatgtgcag     900
atgttggatg tttacagtct aatttctttt gacaatccag atggtggagt ttggaagcaa     960
ggatttgaca ttacttatga atctaatgaa tgggacactg aaccccttca agtctttgtg    1020
```

```
gtgcctcatt cccataacga cccaggttgg ttgaagactt tcaatgacta ctttagagac   1080
aagactcagt atatttttaa taacatggtc ctaaagctga agaagactc acggaggaag    1140 tttatttggt ctgagatctc ttaccttca aagtggtggg atattataga tattcagaag    1200
aaggatgctg ttaaaagttt aatagaaaat ggtcagcttg aaattgtgac aggtggctgg   1260
gttatgcctg atgaagctac tccacattat tttgccttaa ttgatcaact aattgaagga   1320
catcagtggc tggaaaataa tataggagtg aaacctcggt ccggctgggc tattgatccc   1380
tttggacact caccaacaat ggcttatctt ctaaaccgtg ctggactttc tcacatgctt   1440
atccagagag ttcattatgc agttaaaaaa cactttgcac tgcataaaac attggagttt   1500
ttttggagac agaattggga tctgggatct gtcacagata ttttatgcca catgatgccc   1560
ttctacagct atgacatccc tcacacttgt ggacctgatc ctaaaatatg ctgccagttt   1620
gattttaaac gtcttcctgg aggcagattt ggttgtccct ggggagtccc cccagaaaca   1680
atacatcctg gaaatgtcca aagcagggct cggatgctac tagatcagta ccgaaagaag   1740
tcaaagcttt ttcgtaccaa agttctcctg gctccactag gagatgattt ccgctactgt   1800
gaatacacgg aatgggattt acagtttaag aattatcagc agcttttga ttatatgaat    1860 tctcagtcca gtttaaagt taagatacag tttggaactt tatcagattt ttttgatgcg   1920
ctggataaag cagatgaaac tcagagagac aagggccagt cgatgttccc tgttttaagt   1980 ggagatttt tcacttatgc cgatcgagat gatcattact ggagtggcta ttttacatcc    2040
agaccttttt acaaacgaat ggacagaatc atggaatctc atttaagggc tgctgaaatt   2100
ctttactatt tcgccctgag acaagctcac aaatacaaga taaataaatt tctctcatca   2160
tcactttaca cggcactgac agaagccaga aggaatttgg gactgtttca acatcatgat   2220
gctatcacag gaactgcaaa agactgggtg gttgtggatt atggtaccag acttttcat    2280 tcgttaatgg ttttggagaa gataattgga aattctgcat tcttcttat tttgaaggac    2340 aaactcacat acgactctta ctctcctgat accttcctgg agatggattt gaaacaaaaa   2400
tcacaagatt ctctgccaca aaaaaatata ataaggctga gtgcggagcc aaggtacctt   2460
gtggtctata atcctttaga acaagaccga atctcgttgg tctcagtcta tgtgagttcc   2520
ccgacagtgc aagtgttctc tgcttcagga aaacctgtgg aagttcaagt cagcgcagtt   2580
tgggatacag caaatactat ttcagaaaca gcctatgaga tctcttttcg agcacatata   2640
ccgccattgg gactgaaagt gtataagatt ttggaatcag caagttcaaa ttcacattta   2700
gctgattatg tcttgtataa gaataaagta gaagatagcg gaattttcac cataaagaat   2760
atgataaata ctgaagaagg tataacacta gagaactcct ttgttttact tcggtttgat   2820
caaactggac ttatgaagca aatgatgact aaagaagatg gtaaacacca tgaagtaaat   2880
gtgcaatttt catggtatgg aaccacaatt aaaagagaca aaagtggtgc ctacctcttc   2940
ttacctgatg gtaatgccaa gccttatgtt tacacaacac cgcccttttgt cagagtgaca   3000 catggaagga tttattcgga agtgacttgc ttttttgacc atgttactca tagagtccga   3060
ctataccaca tacagggaat agaaggacag tctgtggaag tttccaatat tgtggacatc   3120
cgaaaagtat ataaccgtga gattgcaatg aaaatttctt ctgatataaa agccaaaat    3180 agattttata ctgacctaaa tgggtaccag attcaaccta gaatgacact gagcaaattg   3240
cctcttcaag caaatgtcta tcccatgacc acaatggcct atatccagga tgccaaacat   3300
cgtttgacac tgctctctgc tcagtctta ggggtttcga gtttgaatag tggtcagatt    3360
```

| | |
|---|---:|
| gaagttatca tggatcgaag actcatgcaa gatgataatc gtggccttga gcaaggtatc | 3420 |
| caggataaca agattacagc taatctattt cgaatactac tagaaaaaag aagtgctgtt | 3480 |
| aatacggaag aagaaaagaa gtcggtcagt tatccttctc tccttagcca cataacttct | 3540 |
| tctctcatga atcatccagt cattccaatg gcaaataagt tctcacctac ccttgagctg | 3600 |
| caaggtgaat tctctccatt acagtcatct ttgccttgtg acattcatct ggttaatttg | 3660 |
| agaacaatac agtcaaggt gggcaatggg cactccaatg aggcagcctt gatcctccac | 3720 |
| agaaaagggt ttgattgtcg gttctctagc aaaggcacag gctgttttg ttctactact | 3780 |
| cagggaaaga tattggtaca gaacttttta aacaagttta ttgtcgaaag tctcacacct | 3840 |
| tcatcactat ccttgatgca ttcacctccc ggcactcaga atataagtga gatcaacttg | 3900 |
| agtccaatgg aaatcagcac attccgaatc cagttgaggt gaacctgact ttcacatttg | 3960 |
| gattgagaat cattggcttt tataccttc ttggtttgac gtgcaataaa gaagcacatt | 4020 |
| attttagctt ctggctactg tgagaacatg aattctgtga ttctgtgggt tttttctttt | 4080 |
| ttcttttacc agtacagtaa g | 4101 |

<210> SEQ ID NO 2
<211> LENGTH: 3599
<212> TYPE: DNA
<213> ORGANISM: Homo sapiens

<400> SEQUENCE: 2

| | |
|---|---:|
| aaaatgaagt taagccgcca gttcaccgtg ttcggcagtg cgatcttctg tgtggtgatt | 60 |
| ttctcgctct acctgatgct ggaccggggt cacttagact accccaggaa cccgcgccgc | 120 |
| gagggctcct tccctcaggg ccagctctca atgttgcaag aaaaaataga ccatttggag | 180 |
| cgtttgctag ctgagaataa tgagatcatc tcaaatatta gagactcagt catcaatttg | 240 |
| agtgagtctg tggaggatgg tccgaaaagt tcacaaagca atttcagcca aggtgctggc | 300 |
| tcacatcttc tgccctcaca attatccctc tcagttgaca ctgcagactg tctgtttgct | 360 |
| tcacaaagtg gaagtcacaa ttcagatgtg cagatgttgg atgtttacag tctaatttct | 420 |
| tttgacaatc cagatggtgg agtttggaag caaggatttg acattactta tgaatctaat | 480 |
| gaatgggaca ctgaacccct tcaagtcttt gtggtgcctc attcccataa cgacccaggt | 540 |
| tggttgaaga ctttcaatga ctactttaga gacaagactc agtatatttt taataacatg | 600 |
| gtcctaaagc tgaaagaaga ctcacggagg aagtttattt ggtctgagat ctcttacctt | 660 |
| tcaaagtggt gggatattat agatattcag aagaaggatg ctgttaaaag tttaatagaa | 720 |
| aatggtcagc ttgaaattgt gacaggtggc tgggttatgc ctgatgaagc tactccacat | 780 |
| tatttgcct taattgatca actaattgaa ggacatcagt ggctgaaaa taatatagga | 840 |
| gtgaaacctc ggtccggctg ggctattgat cccttggac actcaccaac aatggcttat | 900 |
| cttctaaacc gtgctggact ttctcacatg cttatccaga gagttcatta tgcagttaaa | 960 |
| aaacactttg cactgcataa aacattggag ttttttggga acagaattg ggatctggga | 1020 |
| tctgtcacag atatttatg ccacatgatg ccccttctaca gctatgacat ccctcacact | 1080 |
| tgtggacctg atcctaaaat atgctgccag tttgattta aacgtcttcc tggaggcaga | 1140 |
| tttggttgtc cctggggagt ccccccagaa acaatacatc tggaaatgt ccaaagcagg | 1200 |
| gctcggatgc tactagatca gtaccgaaag aagtcaaagc ttttcgaac caaagttctc | 1260 |
| ctggctccac taggagatga tttccgctac tgtgaataca cggaatggga tttacagtt | 1320 |
| aagaattatc agcagctttt tgattatatg aattctcagt ccaagtttaa agttaagata | 1380 |

```
cagtttggaa ctttatcaga tttttttgat gcgctggata aagcagatga aactcagaga    1440
gacaagggcc aatcgatgtt ccctgtttta agtggagatt ttttcactta tgccgatcga    1500
gatgatcatt actggagtgg ctattttaca tccagaccct tttacaaacg aatggacaga    1560
atcatggaat ctcatttaag ggctgctgaa attctttact atttcgccct gagacaagct    1620
cacaaataca agataaataa atttctctca tcatcacttt acacggcact gacagaagcc    1680
agaaggaatt tgggactgtt tcaacatcat gatgctatca caggaactgc aaaagactgg    1740
gtggttgtgg attatggtac cagacttttt cattcgttaa tggttttgga agagataatt    1800
ggaaattctg catttcttct tattgggaag acaaactca catacgactc ttactctcct    1860
gataccttcc tggagatgga tttgaaacaa aaatcacaag attctctgcc acaaaaaaat    1920
ataataaggc tgagtgcgga gccaaggtac cttgtggtct ataatccttt agaacaagac    1980
cgaatctcgt tggtctcagt ctatgtgagt tccccgacag tgcaagtgtt ctctgcttca    2040
ggaaaacctg tggaagttca agtcagcgca gtttgggata cagcaaatac tatttcagaa    2100
acagcctatg agatctcttt tcgagcacat ataccgccat tgggactgaa agtgtataag    2160
attttggaat cagcaagttc aaattcacat ttagctgatt atgtcttgta taagaataaa    2220
gtagaagata gcggaatttt caccataaag aatatgataa atactgaaga aggtataaca    2280
ctagagaact cctttgtttt acttcggttt gatcaaactg acttatgaa gcaaatgatg    2340 actaaagaag atggtaaaca ccatgaagta aatgtgcaat tttcatggta tggaaccaca    2400
attaaaagag acaaaagtgg tgcctacctc ttcttacctg atggtaatgc caagccttat    2460
gtttacacaa caccgccctt tgtcagagtg acacatggaa ggatttattc ggaagtgact    2520
tgcttttttg accatgttac tcatagagtc cgactatacc acatacaggg aatagaagga    2580
cagtctgtgg aagtttccaa tattgtggac atccgaaaag tatataaccg tgagattgca    2640
atgaaaattt cttctgatat aaaaagccaa aatagatttt atactgacct aaatgggtac    2700
cagattcaac ctagaatgac actgagcaaa ttgcctcttc aagcaaatgt ctatcccatg    2760
accacaatgg cctatatcca ggatgccaaa catcgtttga cactgctctc tgctcagtca    2820
ttaggggttt cgagtttgaa tagtggtcag attgaagtta tcatggatcg aagactcatg    2880
caagatgata atcgtggcct tgagcaaggt atccaggata caagattac agctaatcta    2940 tttcgaatac tactagaaaa aagaagtgct gttaatacgg aagaagaaaa gaagtcggtc    3000
agttatcctt ctctccttag ccacataact tcttctctca tgaatcatcc agtcattcca    3060
atggcaaata agttctcctc acctacccctt gagctgcaag gtgaattctc tccattacag    3120
tcatctttgc cttgtgacat tcatctgctt aatttgagaa caatacagtc aaaggtgggc    3180
aatgggcact ccaatgaggc agccttgatc ctccacagaa aagggtttga ttgtcggttc    3240
tctagcaaag gcacagggct gttttgttct actactcagg gaaagatatt ggtacagaaa    3300
cttttaaaca gtttattgt cgaaagtctc acaccttcat cactatcctt gatgcattca    3360
cctcccggca ctcagaatat aagtgagatc aacttgagtc aatggaaat cagcacattc    3420 cgaatccagt tgaggtgaac ctgactttca catttggatt gagaatcatt ggcttttata    3480
cctttcttgg tttgacgtgc aataaagaag cacattattt tagcttctgg ctactgtgag    3540
aacatgaatt ctgtgattct gtgggttttt tcttttttc ttttaccagt acagtaaga    3599
```

<210> SEQ ID NO 3
<211> LENGTH: 4439
<212> TYPE: DNA

<213> ORGANISM: Homo sapiens

<400> SEQUENCE: 3

```
cactagcgca ttctgcccta caaggcagtg tgaagctact tacatagtat tttcaacagg      60
ttaatccaca cagtgactcc atgaaggaaa taatacaagc attacctcca ttttacaggc     120
aagaaaatag atatttagga agaagaaatt actatcctaa ggtttcacag ttggcacatg     180
atagagtcct cttcttat cttttggaga tctaatgata ccataaatga agggttttcc      240
tatgtgttat ttttatagta catgggcagg gtgttttaaa tgtattgaaa tgaattagaa     300
attttatca tatgatttaa aattgctgtg tgtatcatgt ggtcttgtga tgactcagaa      360
ttccttaaat gactcttctc ttccttcaaa caaaatctta gcagtacccc tacaaaatat     420
cagtgtgaaa caccataaca taggttattc cagccaagac tctgaggtga ggacagcttt    480
aaactgttca ggcacattaa aatcaaatca gtggtggaga ttctggcagc tattcaggaa    540
agatgtctct ttagtacatt aaaaaatctt atcccctagt gaggatgatc aggcgtttgg    600
gcatattcct gtctgtggcc agagaacaga ggaaagaatc agttttatca caatgtcagt    660
gctgagcagc acatgactct tttcaaaaac tgtatgtttc ttaatttttc cagggatttt    720
taattcattt atcataaaca ccttccaact ttaggaaaca aaatgtatta agatgattgt    780
attttaaaat attcagaggc ctaaaccatt catgacattg atacttaaat ggatatgaga    840
aattttattg caagaaaagg tatactgacc ctcttagctg acttgtcatg tttagtattt    900
ttattttttgc ctgcctatca acaatagctt ctgcagtatc aatttaaatg atacatcaag   960
ctggtaaatg tgagctggcc taccaagtga agcataact aaatttaaat agctctgata    1020
taaaataat gaatcagtac atcaaagatt aagaatgcag ttagcaaaaa ttaatgttca    1080
ataagaagc atgtgtgact tttaagttag atggtatgtc attcaatgac cagataagga    1140
ctaagttcag gtgcagttta ttcaactgat gtgtgtgttt gaaaaataag acgaaaacat    1200
aatgctttat ttgaataaac tttaataaaa caatatataa tgtatggaca taaggaaacc    1260
taagtcctcg gggattatag gggaaaccaa ggcatgaggt tacctaacaa ggaaccttag    1320
aacataatct tacctggctc agtacacgta ggagagaatg gtagcaggtg aatgggcagt    1380
gagcatggac ctgaggagaa atgaatttgc ctaactttct tgctaaataa atgtgctttt    1440
ggatgctgac atcgagagag tggtgtgtga agtaccataa atatttgctt tattgtctgc    1500
gcggtgtgac tgcattctgc tcatttgcag gtgggcaatg ggcactccaa tgaggcagcc    1560
ttgatcctcc acagaaaagg gtttgattgt cggttctcta gcaaaggcac agggctgttt    1620
tgttctacta ctcagggaaa gatattggta cagaaacttt taaacaagtt tattgtcgaa    1680
agtctcacac cttcatcact atccttgatg cattcacctc ccggcactca gaatataagt    1740
gagatcaact tgagtccaat ggaaatcagc acattccgaa tccagttgag gtgaacctga    1800
ctttcacatt tggattgaga atcattggct tttataccct tcttggtttg acgtgcaata    1860
aagaagcaca ttattttagc ttctggctac tgtgagaaca tgaattctgt gattctgtgg    1920
gtttttctt ttttcttta ccagtacagt aagaaaaaaa aaaaaaaaa aaaagcatg       1980
ctatcaatca agattctttt tttttaaact ttctcccatg aactaccacc atcagtatga    2040
attgatgcaa caaatgaaga aatatttaaa gacagcctct caacagattg tatctcaggt    2100
taaatgctaa ctaattatgt ctgtgttggg ggttgcgaag agattcttaa aagtatctgt    2160
gtgttgatca tcagttttac aaaaacacct atttggctga aatggaataa atgtttgtg     2220
ggtaaaagct aatggccaaa atggttgcaa tcattcatac tagttagaaa aattatgtgt    2280
```

```
tgaaataagt ggaaaagtgc aatccatcca cccttatgat taacgtagat gattttata      2340 ccttttctg atgtacctct tgaccttctc cttcccttcc tacccttct gagtatttcc        2400 agaaataccct gattttgaat cattcaacag tagaaaaaga ggcatatttt cattacttga     2460
caatgtggga tgggtgcaat ttattccatc ttcactaaaa tagaagcaat tccataggta     2520
ccataaacct attttaggta ccacaaggtg tcttttaca cagctcattt gaatacaggt       2580
gttctgagaa ggggtttcta ttttaaaatt accatatcaa aataaatgtg ccttatttt      2640 ttataagtct tgttaaatca gtgtccatat tactgtttgg ggaaggggga atgttgtggg     2700
gtctgggaga gggtgggtac tttctatgac acataaattg tgtaattttt gcctgacaat     2760
gctggccaca ttctgatctg tttcattaaa tttgtggtga tgttactcta aacattttga    2820
ctatttgaat gtactgagat gtcagaaaac aaaacaagga aggaaaatat tgttaattaa    2880
aatgtgctgc tgccaaggaa actgcaactt gaagcaagga ttttgtaaaa tgcaaaatcc    2940
agctactgtt tccatttcac agtagttaac tatattaaag agagaatgct ttaaaattga    3000 tcttgtttg aaacctactt ttatgtagct catcatggtt tatcttacta aggaatatgt      3060
ttgttcattc agttctcaac ttttgtatgt gctaaccttta aagtgaagtt ctgagcccat    3120
gtgccattac agtgctttta ataaaattta tttgggatta ttgtttcctt aacattaaaa    3180
taatagcgac atttagacta ttcaatttta gcatagaaag gagtctttga gtatgtacag    3240
ttttgaaaat tctcttgag ataattgatt tcatattctg tggctttcaa cctccatta      3300 cctcttgtca ttccaacatc tttatagaga aataaaaacc caatttctct ttcaccattt    3360
agtttgatta tcatctggat tttcactcaa gatgcagctc ctaagattat tgttatgtta    3420
aattcataaa ctccttcacc tttaataatt aaggaaacaa taccagtgtt gataaagata    3480
ttacaagggg taattcatg caataaacat gtaccgtaag ttttcttcca catattttgg     3540 gaaaaacta aaaaagaaa aaggacttcc tttttgtgga catctacaga tgttagggtt      3600
gccagaagca aatcccagga atgagatcag tatttcatt gcatcttaaa tgtataacct    3660
tcctgtggga gttcagtttg tctgtggtta agtgggtgtg cttaatcatt ctcgaaattg    3720
tgatcagatg aaataaaaaa aaaatcttga tgcaataaca gtggttttgc cacttctggt    3780
tgtttgcgat ggatctgtcc catgtcagtc tggggtttta ttcagcttgt gttgctacca   3840
gcagttcaca ggtaaagcag aaattctctt taaccagcaa gtttctgctt tttaaggtta    3900
cttttagaat aaatcatcag ggaaacagag aggatgcttt gctttgggtt gtagtcaaaa    3960
actgattaaa taatttaatg tctctggcac acactaaaaa ccatacactt cagttgtgat    4020
ctcagtggca tatttatttg gttaggtttc gttacattta ttattacaga tgttcagttg    4080
accaagtagt tcagtgtttt ctttcctttt tttggaaatt ttagtttgag tttgtgactg    4140
cagtgttcaa gaactcagca tccttgtttt ctacaaatac tgattaaaat aaaatgctgt    4200
aaaatgtgat gtaaaacatt atcatgatct tcccatgcct ttgttgtact tgtgccgaag    4260
tgttttgata ttcctttgtc tggaagaaaa tgtttgcttt cattttgatc attttgttca   4320
ccttggaatc aacaggtttt gatatttct cttggaagat tttatatctt tttgggaata    4380
tgtaatataa gatctctaat aaagataat cttatcatgt aagaaaaaaa aaaaaaaaa     4439
```

<210> SEQ ID NO 4
<211> LENGTH: 4917
<212> TYPE: DNA
<213> ORGANISM: Homo sapiens

<400> SEQUENCE: 4

```
ggcagctcgg ccgactgggc ccggagcggc gcggaggccg ggcgctgacg gtgtgtgtgg      60
aggccagtat gaagctgaaa aagcaggtga cagtgtgtgg ggctgccatc ttctgtgtgg     120
cagtcttctc gctctacctc atgctggacc gagtgcaaca cgatcccacc cgacaccaga    180
atggtgggaa cttcccccgg agccaaattt ctgtgctgca gaaccgcatt gagcagctgg    240
agcagctttt ggaggagaac catgagatta tcagccatat caaggactcc gtgctggagc    300
tgacagccaa cgcagagggc ccgcccgcca tgctgcccta ctacacggtc aatggctcct    360
gggtggtgcc accggagccc cggcccagct tcttctccat ctccccgcag gactgccagt    420
ttgctttggg gggccggggt cagaagccag agctgcagat gctcactgtg tcggaggagc    480
tgccgtttga caacgtggat ggtggtgtgt ggaggcaagg cttcgacatc tcctacgacc    540
cgcacgactg ggatgctgaa gacctgcagg tgtttgtggt gccccactct cacaatgacc    600
caggctggat caagaccttt gacaagtact acacagagca gacccaacac atcctcaata    660
gcatggtgtc taagctgcag gaggaccccc ggcggcgctt cctctgggca gaggtctcct    720
tcttcgccaa gtggtgggac aacatcaatg tccaaaagag agcggcagtc cgaaggctgg    780
tgggaaacgg gcagctggag attgcgacag gaggctgggt gatgccagat gaggccaatt    840
cccactactt tgcattgatt gaccagctca tcgaaggaca ccagtggctg gagagaaatc    900
ttggtgcaac ccccgctct ggctgggcag tggacccctt ggatacagc tccaccatgc      960
cttacctgct gcgccgtgcc aacctcacca gcatgctgat tcagagagtg cactatgcca   1020
tcaagaagca ctttgctgcc acccacagcc tagagttcat gtggaggcag acatgggact   1080
cggactccag cacagacatc ttctgtcaca tgatgccctt ctacagctat gacgtccccc   1140
atacctgtgg cccagatccc aagatctgct gccaatttga tttcaaacgc ctgcctggtg   1200
ggcgcatcaa ctgcccttgg aaggtgccac cccgggccat cacagaggcc aacgtggcag   1260
agagggcagc cctgcttctg gaccaatacc ggaagaagtc ccagctgttc cgaagcaacg   1320
tcctcctggt gcctcttgga gatgacttcc gatatgacaa gccccaggag tgggatgccc   1380
agttcttcaa ctaccaacgg ctctttgact tcttcaacag caggcctaac ctccatgtgc   1440
aggcccagtt tggcactctt tctgactatt tgatgccct gtacaagagg acaggggtgg   1500
agccagggc ccggcctcca gggtttcctg tgctgagcgg ggatttcttc tcctatgcgg    1560
accgggagga tcattactgg acaggctatt acacttcccg gcccttctac aagagcttag   1620
accgagtcct ggaagcccac ctgcgggggg cagaggttct gtacagcctg gctgcagctc   1680
acgctcgccg ctctggtctg gctggccggt acccactgtc tgatttcacc ctcctgacgg   1740
aagctcggcg cacattgggg ctcttccagc atcacgatgc catcactggc acggccaagg   1800
aggctgtggt ggtggactat ggggtcaggc ttctgcgctc ccttgtcaac ctgaagcagg   1860
tcatcattca tgcagcccac tatctggtgc tgggggacaa ggagacctac cactttgacc   1920
ctgaggcgcc cttcctccaa gtggatgaca ctcgcttaag tcacgacgcc ctcccagagc   1980
gcacggtgat ccagctggat tcctcgccca ggtttgtggt cctattcaac ccactggaac   2040
aggagcgatt cagcatggtg tccctgctgg tcaactctcc ccgcgtgcgt gtcctttcgg   2100
aggagggtca gccctggcc gtgcagatca gcgcacactg gagctctgcc accgaggcgg   2160
tccctgacgt ctaccaggtg tctgtgcctg tccgcctgcc agccctgggc ctgggcgtgc    2220
tgcagctaca gctgggcctg gatgggcacc gcacgctgcc ctcctctgtg cgcatctacc   2280
tgcacggccg gcagctgtcc gtcagcaggc acgaagcgtt tcctctccgt gtcattgact   2340
```

```
ctggcaccag cgacttcgcc ctcagcaacc gctacatgca ggtctggttc tcaggcctta    2400
ctgggctcct caaggggtca gggctgtgtt ttttggcaga gcatccgaag ggtggatgag    2460
gagcacgagc agcaggtgga catgcaggtc cttgtctatg gcacccgtac gtccaaagac    2520
aagagtggag cctacctctt cctgcccgat ggcgaggcaa gccctacgtc cccaaggagc    2580
cccccgtgct gcgtgtcact gaaggccctt tcttctcaga ggtggttgcg tactatgagc    2640
acattcacca ggcggtccgg ctttacaatc tgccaggggt ggaggggctg tctctggaca    2700
tatcatccct ggtggacatc cgggactacg tcaacaagga gctggccctg cacatccata    2760
cagacatcga cagccagggt gcagccccga cggtatctga agaagctccc cctccaggcc    2820
aacttctacc ccatgccagt catggcctat atccaggacg cacagaagcg cctcacgctg    2880
cacactgccc aggccctggg tgtctctagc ctcaaagatg gccagctgga ggtgatcttg    2940
gaccggcggc tgatgcagga tgacaaccgg ggcctaggcc aagggctcaa ggacaacaag    3000
agaacctgca accgtttccg cctcctgcta gagcggcgaa ccgtgggcag tgaggtccaa    3060
gatagccact ctaccagcta cccatccctc ctcagccacc tgacctccat gtacctgaac    3120
gccccggcgc tcgctctgcc tgtagccagg atgcagctcc caggccctgg tctgcgctca    3180
tttcatcctc tggcttcctc actgcccgt gacttccacc tgctcaacct acgtacgctc    3240
caggctgagg aggacaccct accctcggcg agaccgcac tcatcttaca ccgcaagggt    3300
tttgactgcg gcctggaggc caagaacttg ggcttcaact gcaccacaag ccaaggcaag    3360
gtagccctgg gcagccttt ccatggcctg gatgtggtat tccttcagcc aacctccttg    3420
acgttactgt accctctggc ctccccgtcc aacagcactg acgtctattt ggagcccatg    3480
gagattgcta cctttcgcct ccgcttgggt tagggcttct tgtggcctga agagaaagtt    3540
cattcacaga gactgcctct taacatgaag atcattggac aagccacacg ggtatcccat    3600
cccgatctgc ctcccagaac tgtgacacac tgggctctgc cctcattttc tgtttattgc    3660
tgctgctgtg ttttcggcgc aacccacaaa cccagtgatg ggtaaatagg gcagacgcca    3720
gtgagatcag ggagagaagg cccttggtca gagtgggcag tgccaggctc tgctttgggt    3780
tgtgagtgga cacccaactg ggcacaggct caggcaccca tcctttttcc aaacagggat    3840
atagaagtgg tggaagcaga cagaagaggt aaggagggct aagtgggtaa cagcccagca    3900
tcagggtcac tgtggcaaca gcaggctcta ggggaatcct gtggttatgt agagactcca    3960
tgtcctggtg tgatgagcag gatcagagtg actctgggag gacaggggtg gggacccaga    4020
gttagcagtg gggatggagc agtagaagga atcactgttt ctcctaggag tctgaaggcc    4080
tcgctgcttt ctgtgatggc tttgcagtaa gtgccgcctg gcctgcatgc attggctaac    4140
aggctgcaga atggcaggaa ggactcgcta gagattgtca tggccagaga tcataggtca    4200
cttcaggtag caagacccct ggcaaactgg gcacttggcc tatgtactga tttgtgggat    4260
ggtggcaggg gtgtggggtc cttcaccctg cctgaattct ctttggcttc tgtgctctgt    4320
atgctgctgt ccccaagggc tctttcttat tatggcaggg agtggggatt ggtcctactt    4380
tctttctctg gaaaggaaag cctccaagac tccatgtgct gggcagctt gagaaggcgt    4440 tcagcaccac gcctagcagg cagaccttga agcctcacct ttagtctatc tgcagaggta    4500
ttcagttcct ggcacagggg actaggggca tgtagagtat atgaggaggc agtatggctg    4560
tgcaggagcc ttcatttcag cttcaattaa tagggaagaa tttatgatag ctctatagat    4620
gctgaaaagg tatttcgtaa gatttaaaat ccatccctta ttaaaactct tagtaaatta    4680
```

```
agtctggaaa gaaacaccct aatctagata aaggtctgtt tcagaaacca acagtgatgg    4740
cattctaaag agtcagacgc cacaggcatt cccattaaag tcagaaacta gccaagggca    4800
agctattatt cagcagtgtc ccggcactac taacccctgc aacaagccag atgaggaaca    4860
taaggaagaa ttataattgt cattatttgt agacaataaa actgcctacc tgtaaaa      4917
```

<210> SEQ ID NO 5
<211> LENGTH: 1143
<212> TYPE: PRT
<213> ORGANISM: Homo sapiens

<400> SEQUENCE: 5

```
Met Lys Leu Ser Arg Gln Phe Thr Val Phe Gly Ser Ala Ile Phe Cys
1               5                   10                  15

Val Val Ile Phe Ser Leu Tyr Leu Met Leu Asp Arg Gly His Leu Asp
            20                  25                  30

Tyr Pro Arg Asn Pro Arg Arg Glu Gly Ser Phe Pro Gln Gly Gln Leu
        35                  40                  45

Ser Met Leu Gln Glu Lys Ile Asp His Leu Glu Arg Leu Leu Ala Glu
    50                  55                  60

Asn Asn Glu Ile Ile Ser Asn Ile Arg Asp Ser Val Ile Asn Leu Ser
65                  70                  75                  80

Glu Ser Val Glu Asp Gly Pro Lys Ser Ser Gln Ser Asn Phe Ser Gln
                85                  90                  95

Gly Ala Gly Ser His Leu Leu Pro Ser Gln Leu Ser Leu Ser Val Asp
            100                 105                 110

Thr Ala Asp Cys Leu Phe Ala Ser Gln Ser Gly Ser His Asn Ser Asp
        115                 120                 125

Val Gln Met Leu Asp Val Tyr Ser Leu Ile Ser Phe Asp Asn Pro Asp
    130                 135                 140

Gly Gly Val Trp Lys Gln Gly Phe Asp Ile Thr Tyr Glu Ser Asn Glu
145                 150                 155                 160

Trp Asp Thr Glu Pro Leu Gln Val Phe Val Pro His Ser His Asn
                165                 170                 175

Asp Pro Gly Trp Leu Lys Thr Phe Asn Asp Tyr Phe Arg Asp Lys Thr
            180                 185                 190

Gln Tyr Ile Phe Asn Asn Met Val Leu Lys Leu Glu Asp Ser Arg
        195                 200                 205

Arg Lys Phe Ile Trp Ser Glu Ile Ser Tyr Leu Ser Lys Trp Trp Asp
    210                 215                 220

Ile Ile Asp Ile Gln Lys Lys Asp Ala Val Lys Ser Leu Ile Glu Asn
225                 230                 235                 240

Gly Gln Leu Glu Ile Val Thr Gly Gly Trp Val Met Pro Asp Glu Ala
                245                 250                 255

Thr Pro His Tyr Phe Ala Leu Ile Asp Gln Leu Ile Glu Gly His Gln
            260                 265                 270

Trp Leu Glu Asn Asn Ile Gly Val Lys Pro Arg Ser Gly Trp Ala Ile
        275                 280                 285

Asp Pro Phe Gly His Ser Pro Thr Met Ala Tyr Leu Leu Asn Arg Ala
    290                 295                 300

Gly Leu Ser His Met Leu Ile Gln Arg Val His Tyr Ala Val Lys Lys
305                 310                 315                 320

His Phe Ala Leu His Lys Thr Leu Glu Phe Phe Trp Arg Gln Asn Trp
                325                 330                 335
```

-continued

```
Asp Leu Gly Ser Val Thr Asp Ile Leu Cys His Met Met Pro Phe Tyr
            340                 345                 350

Ser Tyr Asp Ile Pro His Thr Cys Gly Pro Asp Pro Lys Ile Cys Cys
        355                 360                 365

Gln Phe Asp Phe Lys Arg Leu Pro Gly Arg Phe Gly Cys Pro Trp
    370                 375                 380

Gly Val Pro Pro Glu Thr Ile His Pro Gly Asn Val Gln Ser Arg Ala
385                 390                 395                 400

Arg Met Leu Leu Asp Gln Tyr Arg Lys Lys Ser Lys Leu Phe Arg Thr
                405                 410                 415

Lys Val Leu Leu Ala Pro Leu Gly Asp Asp Phe Arg Tyr Cys Glu Tyr
                420                 425                 430

Thr Glu Trp Asp Leu Gln Phe Lys Asn Tyr Gln Gln Leu Phe Asp Tyr
            435                 440                 445

Met Asn Ser Gln Ser Lys Phe Lys Val Lys Ile Gln Phe Gly Thr Leu
    450                 455                 460

Ser Asp Phe Phe Asp Ala Leu Asp Lys Ala Asp Glu Thr Gln Arg Asp
465                 470                 475                 480

Lys Gly Gln Ser Met Phe Pro Val Leu Ser Gly Asp Phe Phe Thr Tyr
                485                 490                 495

Ala Asp Arg Asp Asp His Tyr Trp Ser Gly Tyr Phe Thr Ser Arg Pro
            500                 505                 510

Phe Tyr Lys Arg Met Asp Arg Ile Met Glu Ser His Leu Arg Ala Ala
        515                 520                 525

Glu Ile Leu Tyr Tyr Phe Ala Leu Arg Gln Ala His Lys Tyr Lys Ile
    530                 535                 540

Asn Lys Phe Leu Ser Ser Ser Leu Tyr Thr Ala Leu Thr Glu Ala Arg
545                 550                 555                 560

Arg Asn Leu Gly Leu Phe Gln His His Asp Ala Ile Thr Gly Thr Ala
                565                 570                 575

Lys Asp Trp Val Val Val Asp Tyr Gly Thr Arg Leu Phe His Ser Leu
            580                 585                 590

Met Val Leu Glu Lys Ile Ile Gly Asn Ser Ala Phe Leu Leu Ile Leu
        595                 600                 605

Lys Asp Lys Leu Thr Tyr Asp Ser Tyr Ser Pro Asp Thr Phe Leu Glu
    610                 615                 620

Met Asp Leu Lys Gln Lys Ser Gln Asp Ser Leu Pro Gln Lys Asn Ile
625                 630                 635                 640

Ile Arg Leu Ser Ala Glu Pro Arg Tyr Leu Val Tyr Asn Pro Leu
                645                 650                 655

Glu Gln Asp Arg Ile Ser Leu Val Ser Val Tyr Val Ser Pro Thr
            660                 665                 670

Val Gln Val Phe Ser Ala Ser Gly Lys Pro Val Glu Val Gln Val Ser
        675                 680                 685

Ala Val Trp Asp Thr Ala Asn Thr Ile Ser Glu Thr Ala Tyr Glu Ile
    690                 695                 700

Ser Phe Arg Ala His Ile Pro Pro Leu Gly Leu Lys Val Tyr Lys Ile
705                 710                 715                 720

Leu Glu Ser Ala Ser Ser Asn Ser His Leu Ala Asp Tyr Val Leu Tyr
                725                 730                 735

Lys Asn Lys Val Glu Asp Ser Gly Ile Phe Thr Ile Lys Asn Met Ile
                740                 745                 750

Asn Thr Glu Glu Gly Ile Thr Leu Glu Asn Ser Phe Val Leu Leu Arg
```

```
                755                 760                 765
Phe Asp Gln Thr Gly Leu Met Lys Gln Met Met Thr Lys Glu Asp Gly
770                 775                 780
Lys His His Glu Val Asn Val Gln Phe Ser Trp Tyr Gly Thr Thr Ile
785                 790                 795                 800
Lys Arg Asp Lys Ser Gly Ala Tyr Leu Phe Leu Pro Asp Gly Asn Ala
                805                 810                 815
Lys Pro Tyr Val Tyr Thr Thr Pro Pro Phe Val Arg Val Thr His Gly
                820                 825                 830
Arg Ile Tyr Ser Glu Val Thr Cys Phe Phe Asp His Val Thr His Arg
                835                 840                 845
Val Arg Leu Tyr His Ile Gln Gly Ile Glu Gly Gln Ser Val Glu Val
850                 855                 860
Ser Asn Ile Val Asp Ile Arg Lys Val Tyr Asn Arg Glu Ile Ala Met
865                 870                 875                 880
Lys Ile Ser Ser Asp Ile Lys Ser Gln Asn Arg Phe Tyr Thr Asp Leu
                885                 890                 895
Asn Gly Tyr Gln Ile Gln Pro Arg Met Thr Leu Ser Lys Leu Pro Leu
                900                 905                 910
Gln Ala Asn Val Tyr Pro Met Thr Thr Met Ala Tyr Ile Gln Asp Ala
                915                 920                 925
Lys His Arg Leu Thr Leu Leu Ser Ala Gln Ser Leu Gly Val Ser Ser
                930                 935                 940
Leu Asn Ser Gly Gln Ile Glu Val Ile Met Asp Arg Arg Leu Met Gln
945                 950                 955                 960
Asp Asp Asn Arg Gly Leu Glu Gln Gly Ile Gln Asp Asn Lys Ile Thr
                965                 970                 975
Ala Asn Leu Phe Arg Ile Leu Leu Glu Lys Arg Ser Ala Val Asn Thr
                980                 985                 990
Glu Glu Glu Lys Lys Ser Val Ser  Tyr Pro Ser Leu Leu  Ser His Ile
                995                 1000                1005
Thr Ser  Ser Leu Met Asn His  Pro Val Ile Pro Met  Ala Asn Lys
    1010                1015                1020
Phe Ser  Pro Thr Leu Glu Leu  Gln Gly Glu Phe Ser  Pro Leu Gln
    1025                1030                1035
Ser Ser  Leu Pro Cys Asp Ile  His Leu Val Asn Leu  Arg Thr Ile
    1040                1045                1050
Gln Ser  Lys Val Gly Asn Gly  His Ser Asn Glu Ala  Ala Leu Ile
    1055                1060                1065
Leu His  Arg Lys Gly Phe Asp  Cys Arg Phe Ser Ser  Lys Gly Thr
    1070                1075                1080
Gly Leu  Phe Cys Ser Thr Thr  Gln Gly Lys Ile Leu  Val Gln Lys
    1085                1090                1095
Leu Leu  Asn Lys Phe Ile Val  Glu Ser Leu Thr Pro  Ser Ser Leu
    1100                1105                1110
Ser Leu  Met His Ser Pro Pro  Gly Thr Gln Asn Ile  Ser Glu Ile
    1115                1120                1125
Asn Leu  Ser Pro Met Glu Ile  Ser Thr Phe Arg Ile  Gln Leu Arg
    1130                1135                1140

<210> SEQ ID NO 6
<211> LENGTH: 1139
<212> TYPE: PRT
<213> ORGANISM: Homo sapiens
```

<400> SEQUENCE: 6

```
Met Lys Leu Lys Lys Gln Val Thr Val Cys Gly Ala Ala Ile Phe Cys
1               5                   10                  15
Val Ala Val Phe Ser Leu Tyr Leu Met Leu Asp Arg Val Gln His Asp
            20                  25                  30
Pro Thr Arg His Gln Asn Gly Gly Asn Phe Pro Arg Ser Gln Ile Ser
        35                  40                  45
Val Leu Gln Asn Arg Ile Glu Gln Leu Glu Gln Leu Leu Glu Glu Asn
    50                  55                  60
His Glu Ile Ile Ser His Ile Lys Asp Ser Val Leu Glu Leu Thr Ala
65                  70                  75                  80
Asn Ala Glu Gly Pro Pro Ala Met Leu Pro Tyr Tyr Thr Val Asn Gly
                85                  90                  95
Ser Trp Val Val Pro Glu Pro Arg Pro Ser Phe Phe Ser Ile Ser
            100                 105                 110
Pro Gln Asp Cys Gln Phe Ala Leu Gly Gly Arg Gly Gln Lys Pro Glu
        115                 120                 125
Leu Gln Met Leu Thr Val Ser Glu Glu Leu Pro Phe Asp Asn Val Asp
    130                 135                 140
Gly Gly Val Trp Arg Gln Gly Phe Asp Ile Ser Tyr Asp Pro His Asp
145                 150                 155                 160
Trp Asp Ala Glu Asp Leu Gln Val Phe Val Pro His Ser His Asn
                165                 170                 175
Asp Pro Gly Trp Ile Lys Thr Phe Asp Lys Tyr Tyr Thr Glu Gln Thr
            180                 185                 190
Gln His Ile Leu Asn Ser Met Val Ser Lys Leu Gln Glu Asp Pro Arg
        195                 200                 205
Arg Arg Phe Leu Trp Ala Glu Val Ser Phe Phe Ala Lys Trp Trp Asp
    210                 215                 220
Asn Ile Asn Val Gln Lys Arg Ala Ala Val Arg Arg Leu Val Gly Asn
225                 230                 235                 240
Gly Gln Leu Glu Ile Ala Thr Gly Gly Trp Val Met Pro Asp Glu Ala
                245                 250                 255
Asn Ser His Tyr Phe Ala Leu Ile Asp Gln Leu Ile Glu Gly His Gln
            260                 265                 270
Trp Leu Glu Arg Asn Leu Gly Ala Thr Pro Arg Ser Gly Trp Ala Val
        275                 280                 285
Asp Pro Phe Gly Tyr Ser Ser Thr Met Pro Tyr Leu Leu Arg Arg Ala
    290                 295                 300
Asn Leu Thr Ser Met Leu Ile Gln Arg Val His Tyr Ala Ile Lys Lys
305                 310                 315                 320
His Phe Ala Ala Thr His Ser Leu Glu Phe Met Trp Arg Gln Thr Trp
                325                 330                 335
Asp Ser Asp Ser Ser Thr Asp Ile Phe Cys His Met Met Pro Phe Tyr
            340                 345                 350
Ser Tyr Asp Val Pro His Thr Cys Gly Pro Asp Pro Lys Ile Cys Cys
        355                 360                 365
Gln Phe Asp Phe Lys Arg Leu Pro Gly Gly Arg Ile Asn Cys Pro Trp
    370                 375                 380
Lys Val Pro Pro Arg Ala Ile Thr Glu Ala Asn Val Ala Glu Arg Ala
385                 390                 395                 400
Ala Leu Leu Leu Asp Gln Tyr Arg Lys Lys Ser Gln Leu Phe Arg Ser
```

-continued

```
                405                 410                 415
Asn Val Leu Leu Val Pro Leu Gly Asp Asp Phe Arg Tyr Asp Lys Pro
                420                 425                 430
Gln Glu Trp Asp Ala Gln Phe Phe Asn Tyr Gln Arg Leu Phe Asp Phe
                435                 440                 445
Phe Asn Ser Arg Pro Asn Leu His Val Gln Ala Gln Phe Gly Thr Leu
        450                 455                 460
Ser Asp Tyr Phe Asp Ala Leu Tyr Lys Arg Thr Gly Val Glu Pro Gly
465                 470                 475                 480
Ala Arg Pro Pro Gly Phe Pro Val Leu Ser Gly Asp Phe Phe Ser Tyr
                485                 490                 495
Ala Asp Arg Glu Asp His Tyr Trp Thr Gly Tyr Tyr Thr Ser Arg Pro
                500                 505                 510
Phe Tyr Lys Ser Leu Asp Arg Val Leu Glu Ala His Leu Arg Gly Ala
                515                 520                 525
Glu Val Leu Tyr Ser Leu Ala Ala His Ala Arg Arg Ser Gly Leu
                530                 535                 540
Ala Gly Arg Tyr Pro Leu Ser Asp Phe Thr Leu Leu Thr Glu Ala Arg
545                 550                 555                 560
Arg Thr Leu Gly Leu Phe Gln His His Asp Ala Ile Thr Gly Thr Ala
                565                 570                 575
Lys Glu Ala Val Val Asp Tyr Gly Val Arg Leu Leu Arg Ser Leu
                580                 585                 590
Val Asn Leu Lys Gln Val Ile His Ala Ala His Tyr Leu Val Leu
                595                 600                 605
Gly Asp Lys Glu Thr Tyr His Phe Asp Pro Glu Ala Pro Phe Leu Gln
                610                 615                 620
Val Asp Thr Arg Leu Ser His Asp Ala Leu Pro Glu Arg Thr Val
625                 630                 635                 640
Ile Gln Leu Asp Ser Ser Pro Arg Phe Val Leu Phe Asn Pro Leu
                645                 650                 655
Glu Gln Glu Arg Phe Ser Met Val Ser Leu Leu Val Asn Ser Pro Arg
                660                 665                 670
Val Arg Val Leu Ser Glu Glu Gly Gln Pro Leu Ala Val Gln Ile Ser
                675                 680                 685
Ala His Trp Ser Ser Ala Thr Glu Ala Val Pro Asp Val Tyr Gln Val
                690                 695                 700
Ser Val Pro Val Arg Leu Pro Ala Leu Gly Leu Gly Val Leu Gln Leu
705                 710                 715                 720
Gln Leu Gly Leu Asp Gly His Arg Thr Leu Pro Ser Ser Val Arg Ile
                725                 730                 735
Tyr Leu His Gly Arg Gln Leu Ser Val Ser Arg His Glu Ala Phe Pro
                740                 745                 750
Leu Arg Val Ile Asp Ser Gly Thr Ser Asp Phe Ala Leu Ser Asn Arg
                755                 760                 765
Tyr Met Gln Val Trp Phe Ser Gly Leu Thr Gly Leu Leu Lys Ser Ile
                770                 775                 780
Arg Arg Val Asp Glu Glu His Glu Gln Gln Val Asp Met Gln Val Leu
785                 790                 795                 800
Val Tyr Gly Thr Arg Thr Ser Lys Asp Lys Ser Gly Ala Tyr Leu Phe
                805                 810                 815
Leu Pro Asp Gly Glu Ala Ser Pro Thr Ser Pro Arg Ser Pro Pro Cys
                820                 825                 830
```

```
                    -continued

Cys Val Ser Leu Lys Ala Leu Ser Ser Gln Arg Trp Leu Arg Thr Met
        835             840             845

Ser Thr Phe Thr Arg Arg Ser Gly Phe Thr Ile Cys Gln Gly Trp Arg
    850             855             860

Gly Cys Leu Trp Thr Tyr His Pro Trp Trp Thr Ser Gly Thr Thr Ser
865             870             875             880

Thr Arg Ser Trp Pro Cys Thr Ser Ile Gln Thr Ser Thr Ala Arg Val
                885             890             895

Gln Pro Arg Arg Tyr Leu Lys Lys Leu Pro Leu Gln Ala Asn Phe Tyr
            900             905             910

Pro Met Pro Val Met Ala Tyr Ile Gln Asp Ala Gln Lys Arg Leu Thr
        915             920             925

Leu His Thr Ala Gln Ala Leu Gly Val Ser Ser Leu Lys Asp Gly Gln
    930             935             940

Leu Glu Val Ile Leu Asp Arg Arg Leu Met Gln Asp Asn Arg Gly
945             950             955             960

Leu Gly Gln Gly Leu Lys Asp Asn Lys Arg Thr Cys Asn Arg Phe Arg
                965             970             975

Leu Leu Leu Glu Arg Arg Thr Val Gly Ser Glu Val Gln Asp Ser His
            980             985             990

Ser Thr Ser Tyr Pro Ser Leu Leu Ser His Leu Thr Ser Met Tyr Leu
        995             1000            1005

Asn Ala Pro Ala Leu Ala Leu Pro Val Ala Arg Met Gln Leu Pro
    1010            1015            1020

Gly Pro Gly Leu Arg Ser Phe His Pro Leu Ala Ser Ser Leu Pro
    1025            1030            1035

Cys Asp Phe His Leu Leu Asn Leu Arg Thr Leu Gln Ala Glu Glu
    1040            1045            1050

Asp Thr Leu Pro Ser Ala Glu Thr Ala Leu Ile Leu His Arg Lys
    1055            1060            1065

Gly Phe Asp Cys Gly Leu Glu Ala Lys Asn Leu Gly Phe Asn Cys
    1070            1075            1080

Thr Thr Ser Gln Gly Lys Val Ala Leu Gly Ser Leu Phe His Gly
    1085            1090            1095

Leu Asp Val Val Phe Leu Gln Pro Thr Ser Leu Thr Leu Leu Tyr
    1100            1105            1110

Pro Leu Ala Ser Pro Ser Asn Ser Thr Asp Val Tyr Leu Glu Pro
    1115            1120            1125

Met Glu Ile Ala Thr Phe Arg Leu Arg Leu Gly
    1130            1135
```